(12) United States Patent
Altmann et al.

(10) Patent No.: US 6,350,878 B1
(45) Date of Patent: Feb. 26, 2002

(54) INTERMEDIATES FOR THE SYNTHESIS OF EPOTHILONES AND METHODS FOR THEIR PREPARATION

(75) Inventors: Karl-Heinz Altmann, Reinach (CH); Armin Bauer, Frankfurt; Dieter Schinzer, Braunschweig, both of (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/715,674

(22) Filed: Nov. 17, 2000

Related U.S. Application Data

(63) Continuation of application No. PCT/EP99/05354, filed on May 14, 1999.

(30) Foreign Application Priority Data

May 18, 1998 (GB) .............................................. 9810659

(51) Int. Cl.⁷ .................... C07D 231/00; C07D 277/22; C07D 277/30; C07D 307/02
(52) U.S. Cl. ...................... 548/110; 548/203; 548/204; 549/476
(58) Field of Search ................................ 548/110, 203, 548/204; 549/476

(56) References Cited

U.S. PATENT DOCUMENTS

| | | | |
|---|---|---|---|
| 5,969,145 A | 10/1999 | Schinzer et al. | |
| 6,211,412 B1 * | 4/2001 | Georg et al. ................. | 568/309 |
| 6,262,094 B1 * | 7/2001 | Hoefle et al. ................ | 514/365 |
| 6,284,781 B1 * | 9/2001 | Danishefsky et al. ........ | 514/365 |

FOREIGN PATENT DOCUMENTS

| | | |
|---|---|---|
| WO | WO 97/19086 | 5/1997 |
| WO | WO 98/08849 | 3/1998 |
| WO | WO 98/25929 | 6/1998 |
| WO | WO 99/54318 | 10/1999 |
| WO | WO 99/54319 | 10/1999 |
| WO | WO 99/54330 | 10/1999 |
| WO | WO 99/58534 | 11/1999 |
| WO | WO 99/65913 | 12/1999 |
| WO | WO 00/00485 | 1/2000 |

OTHER PUBLICATIONS

Nicolaou K.C. et al., Eur.J.Chem., vol. 3, No. 12, pp. 1971–1986 (1997).
Nicolaou K.C. et al., Chem.Commun., vol. 24, pp. 2343–2344 (1997).
Nicolaou K.C. et al., Nature, vol. 390, No. 6, p. 100 (1997).
Nicolaou K.C. et al., J.Am.Chem.Soc., vol. 119, No. 34, pp. 7974–7991 (1997).
Nicolaou K.C. et al., Nature, vol. 387, pp. 268–272 (1997).
Schinzer D. et al., Eur.J.Chem., vol. 2, No. 11, pp. 1477–1482 (1996).
Schinzer D. et al., Synlett, vol. 8, pp. 861–864 (1998).
Balog A. et al., Angew.Chem.Int.Ed., vol. 37, No. 19, pp. 2675–2678 (1998).
Mulzer J. et al., Tetrahedron Letters, vol. 39, No. 47, pp. 8633–8636 (1998).
Sefkow M. et al., Bioorganic & Medicinal Chemistry Letters, vol. 8, pp. 3025–3030 (1998).
Derwent Abstract 1997–310273 (WO 97/19086).
Derwent Abstract 2000–160660 (WO 00/00485).
Derwent Abstract 2000–272167 (WO 99/65916).
Derwent Abstract 2000–014254 (WO 99/58534).

* cited by examiner

*Primary Examiner*—Deborah C. Lambkin
(74) *Attorney, Agent, or Firm*—Joseph J. Borovian

(57) ABSTRACT

The invention relates to a method of synthesis for a compound of formula (I),

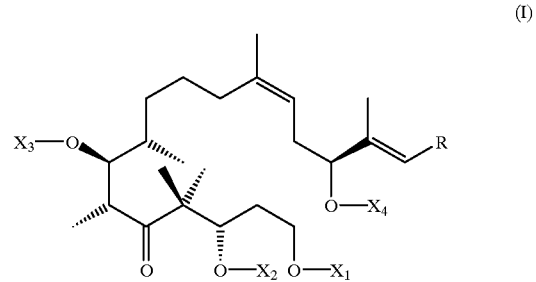

wherein R is a heterocyclyl moiety and $X_1$, $X_2$, $X_3$ and $X_4$ are, independently of each other, protecting groups, which is appropriate for the synthesis of epothilone B and desoxyepothione B.

9 Claims, No Drawings

INTERMEDIATES FOR THE SYNTHESIS OF EPOTHILONES AND METHODS FOR THEIR PREPARATION

This is a continuation of International Application No. PCT/EP 99/03354, filed Apr. 14, 1999, the contents of which are incorporated herein by reference.

SUMMARY OF THE INVENTION

The invention relates to a new method of synthesis of an intermediate useful for the synthesis of epothilone B and desoxyepothilone B and derivatives thereof, as well as to certain new partial reaction sequences for the production of key intermediates.

BACKGROUND OF THE INVENTION

Among cytotoxic agents for the treatment of tumors, Taxol® (Paclitaxel), a microtubule stabilizing agent, has become a very important compound with a remarkable economic success (see McGuire, W. P., et al., Ann. Int. Med. 111, 273–9 (1989)).

Taxol® has a number of disadvantages. Especially its extremely low solubility in water represents a severe problem. It has become necessary to administer Taxol in a formulation with Cremophor EL® (polyoxyethylated castor oil; BASF, Ludwigshafen, Germany) which has severe side effects, causing inter alia allergic reactions that in one case even were reported to have led to the death of a patient. More severely, certain tumor types are known to be refractory against treatment with Taxol®.

Taxol® treatment is associated with a number of significant side effects and some major classes of solid tumors, namely colon and prostate, are poorly responsive to this compound (see Rowinsky E. K., loc. cit.).

The epothilones A and B are a new class of microtubule stabilizing cytotoxic agents (see Gerth, K. et al., J. Antibiot. 49, 560–3 (1966); Hoefle et al., DE 41 38 042) of the formulae:

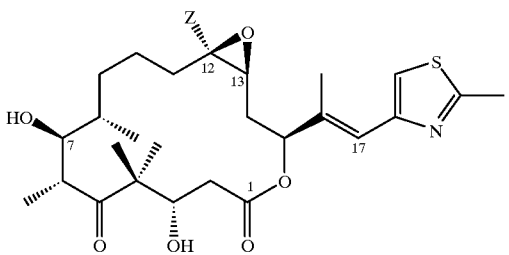

wherein Z is hydrogen (epothilone A) or methyl (epothilone B).

These compounds have the following advantages:
(i) they show better water solubility than Taxol and are thus more appropriate for formulation; and
(ii) they have been reported to be active also against the proliferation of cells that, due to the activity of the P-glycoprotein efflux pump which renders them multidrug resistant, show resistance to the treatment with other chemotherapeutics, e.g. Taxol (see Bollag, D. M., et al., "Epothilones, a new class of microtubule-stabilizing agents with a Taxol-like mechanism of action", Cancer Research 55, 2325–33 (1995); and Bollag D. M., Exp. Opin. Invest. Drugs 6, 867–73 (1997); and (iii) despite apparently sharing the same, or at least a largely overlapping binding site on the microtubule, the epothilones have been shown to be active against a Taxot®-resistant ovarian carcinoma cell line with an altered β-tubulin (see Kowalski, R. J., et al., J. Biol. Chem. 272(4), 2534–2541 (1997)).

Due to their impressive biological profile, multiple initial efforts towards the synthesis of epothilones appeared almost simultaneously in the literature. Three groups described total syntheses of epothilone A, and two total syntheses of epothilone B appeared concurrently as well. In addition, a flood of papers appeared which presented partial solutions towards the synthesis of epothilones. Since these studies, many derivatives have been synthesized and their biological profiles have been tested.

Especially epothilone B provides important biological properties that are exemplary for other epothilones:

Epothilone B is appropriate preferably in the treatment of proliferative diseases, such as of gastrointestinal tumors, more preferably (1) a tumor of the colon AND/OR the rectum (colorectal tumor), especially if it is refractory to a (meaning at least one) representative of the taxane class of anti-cancer agents, in particular paclitaxel, AND/OR at least one standard treatment with an other chemotherapeutic, especially 5-fluorouracil; (2) a tumor of the genitourinary tract, more preferably a tumor of the prostate, including primary and metastatic tumors, especially if refractory to hormone treatment ("hormone refractory prostate cancer") and/or treatment with other standard chemotherapeutics; (3) an epidermoid tumor, more preferably an epidermoid head and neck tumor, most preferably a mouth tumor; (4) a lung tumor, more preferably a non-small cell lung tumor, especially any of these tumors that is refractory to treatment with one or more other chemotherapeutics (especially due to multidrug resistance), especially to treatment with a member of the taxane class of anti-cancer agents, in particular TAXOL®; or (5) a breast tumor, more preferably one that is multidrug resistant, especially refractory to treatment with a member of the taxane class of anti-cancer agents, in particular TAXOL®; relating especially also to the treatment of a multidrug resistant lung tumor (preferably a non-small cell lung tumor), a multidrug resistant breast tumor, or a multidrug resistant epidermoid tumor, or in a broader sense of the invention to a treatment schedule for the treatment of an aforementioned or (in a broader sense of the invention) any other tumor.

Epothilone B is preferably used weekly or three-weekly; preferably for weekly treatment the dose is between about 0.1 and about 6, preferably about 0.1 and about 5 mg/m$^2$, more preferably about 0.1 and about 3 mg/m$^2$, even more preferably 0.1 and 1.7 mg/m$^2$, most preferably about 0.3 and about 1 mg/m$^2$; for three-weekly treatment (treatment every three weeks or every third week) the dose is between about 0.3 and about 18 mg/m$^2$, preferably about 0.3 and about 15 mg/m$^2$, more preferably about 0.3 and about 12 mg/m$^2$, even more preferably about 0.3 and about 7.5 mg/m$^2$, still more preferably about 0.3 and about 5 mg/M$^2$, most preferably about 1.0 and about 3.0 mg/m$^2$. This dose is preferably administered to the human by intravenous (i.v.) administration during 2 to 180 min, preferably 2 to 120 min, more preferably during about 5 to about 30 min, most preferably during about 10 to about 30 min, e.g. during about 30 min.

Preferably, especially in the case of weekly treatment, rest periods of more than one week, more preferably of two to ten weeks, more preferably three to six weeks after the preceding treatment may be necessary after for example 3, 4, 6, 8, or more treatment cycles, depending on patient condition, to allow for sufficient recovery from the preceding treatment.

The pharmaceutical compositions comprise from about 0.00002 to about 95%, especially (e.g. in the case of infusion dilutions that are ready for use) of 0.0001 to 0.02%, or (for example in case of infusion concentrates) from about 0.1% to about 95%, preferably from about 20% to about 90%, active ingredient (weight by weight, in each case). Pharmaceutical compositions according to the invention may be, for example, in unit dose form, such as in the form of ampoules, vials, suppositories, dragees, tablets or capsules.

Preferred is an infusion formulation comprising epothilone B and a pharmaceutically acceptable organic solvent. The pharmaceutically acceptable organic solvent used in a formulation according to the invention may be chosen from any such organic solvent known in the art. Preferably the solvent is selected from alcohol, e.g. absolute ethanol or ethanol/water mixtures, more preferably 70% ethanol, polyethylene glycol 300, polyethylene glycol 400, polypropylene glycol or N-methylpyrrolidone, most preferably polypropylene glycol or 70% ethanol or especially polyethylene glycol 300.

Epothilone B may preferably be present in the formulation in a concentration of about 0.1 to about 100 mg/ml, more preferably about 1 to about 100 mg/ml, still more preferably about 1 to about 10 mg/ml (especially in infusion concentrates).

It is a goal of the present invention to provide novel routes to manufacture an intermediate for the synthesis of epothilone B and its predecessor, desoxyepothilone B.

In contrast to a published synthesis by Nicolaou et al. (see J. Am. Chem. Soc. 119, 7974–91 (1997)) for the synthesis of epothilone B, the new route is more convergent, that is, it is based on three rather than two key fragments that have to be assembled to the final product. The disadvantage of the prior art two-fragment strategy consists in the fact that many more steps are required to prepare the individual fragment. Therefore the new synthesis offers large advantages.

DETAILED DESCRIPTION OF THE INVENTION

The invention relates to a formal total synthesis route via an intermediate appropriate for the synthesis of epothilone B and analogues thereof. The approach uses macrolactonization for the final ring closure and provides an especially convergent strategy to obtain the key building blocks.

The invention also especially relates to the synthesis of the aldehyde 17 and the aldehyde 18 (see reaction scheme 2) starting from (+)-malic acid, which is largely unrelated to published synthesis of these compounds and is much more practical.

The invention also especially relates to new processes of manufacture for ethyl ketone 30, either via the ester 26 (scheme 4) or acyl sultam 31. The latter compound has been described in the literature (see Synlett (1997), 623). However, if the procedure recommended in that publication is followed, the wrong (namely the 3R-) enantiomer is obtained instead of the desired isomer 31, which is required for the synthesis of epothilones.

The invention also especially relates to the synthesis of 19 via a Pd-catalyzed coupling reaction, which offers the large advantage of highly selective formation of a cis-bond at the double bond connecting carbon atoms 12 and 13 in epothilone B as well as to the new intermediate 19. This compound has not been described previously as a homogenous double bond isomer at the C12–C13 double bond of epothilone B. Surprisingly, the above reaction is stereoselective only for the methyl substituent Z found in the formula of epothilone B given in the introduction.

The invention relates especially to a new method for the synthesis of an intermediate of the formula I

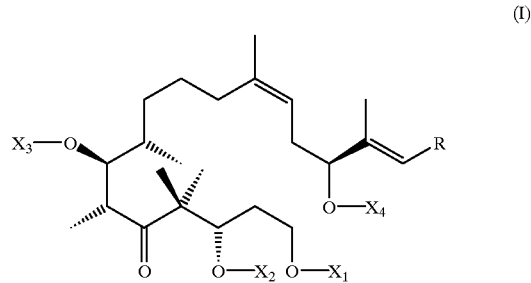

wherein R is a heterocyclyl moiety and $X_1$, $X_2$, $X_3$ and $X_4$ are, independently of each other, protecting groups.

The intermediate of the formula I can then be used for the synthesis of epothilone B and analogues thereof via various steps including macrolactonization and epoxidation, using methods known in the art, see especially Nicolaou et al., J. Am. Chem. Soc. 119, 7974–91 (1997). If the epoxidation step is omitted (and, if present, protecting groups are cleaved of), desoxyepothilone B, the analogue of epothilone B where instead of the oxirane ring a double bond is present, can be synthesized.

Within the present disclosure, the general definitions used hereinbefore and hereinafter preferably have the following meaning, if not indicated otherwise:

A heterocyclyl moiety R is preferably a monocyclic moiety with 5 or 6 ring atoms, wherein 1 to 3, especially one or two, ring carbon atoms each are replaced by a heteroatom selected from nitrogen, oxygen or sulfur; the heterocyclic moiety may be unsubstituted or substituted by one or more substituents that are preferably independently selected from the group consisting of oxo, lower alkyl, especially methyl, hydroxy-lower alkyl, especially hydroxymethyl, lower alkylmercapto, especially methylmercapto, phenylmercapto, amino, mono- or di-lower. alkylamino, especially dimethylamino, halogen-lower alkyl, such as fluoromethyl, or acyloxy-lower alkyl, such as lower alkanoyloxy-lower alkyl, e.g. 5-acetyloxy-pentyl or acetyloxymethyl.

Most preferably, the heterocyclyl moiety has any one of the following formulae:

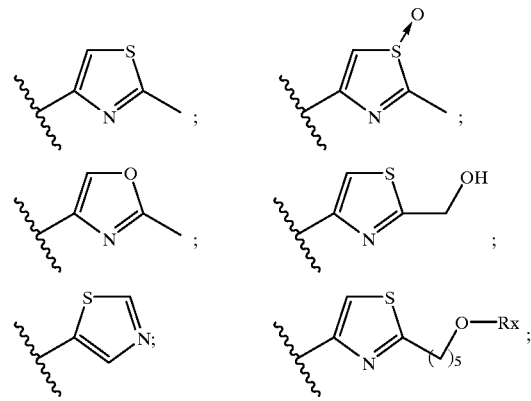

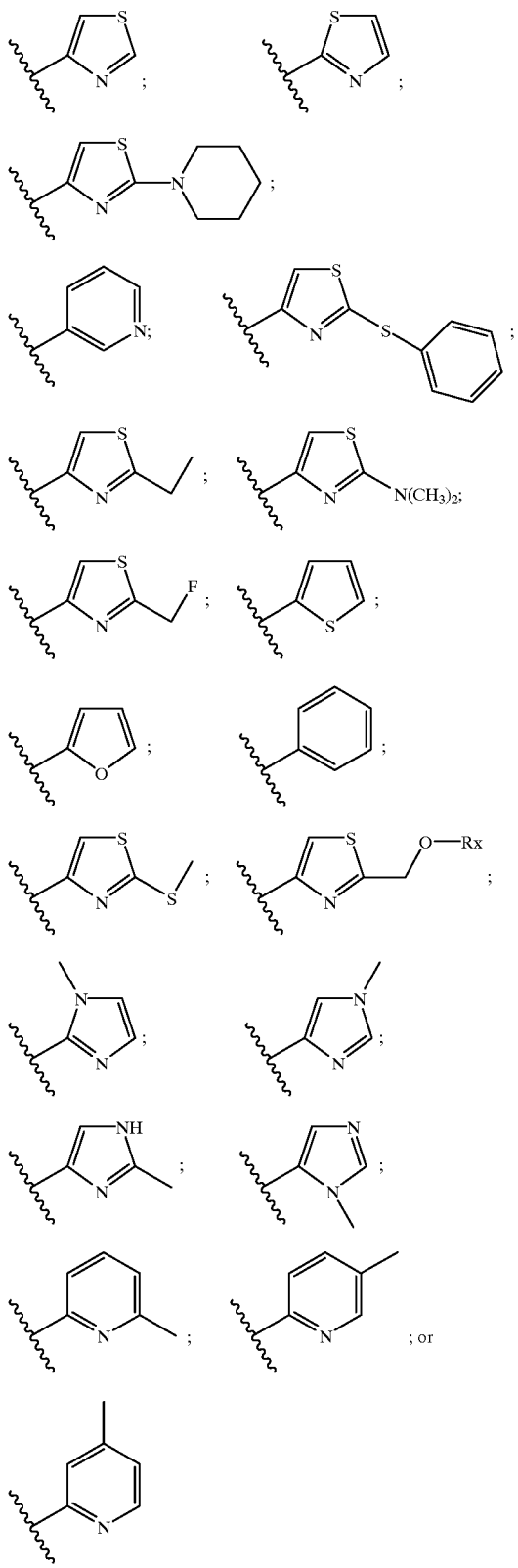

wherein Rx is acyl, especially lower alkanoyl, such as acetyl;

Most preferably, the moiety R has the formula I

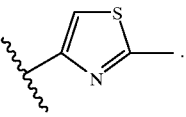

A protecting group is especially selected from the group comprising a silyl protecting group, especially diaryl-lower alkyl-silyl, such as diphenyl-tert-butylsilyl, or more preferably tri-lower alkylsilyl, such as tert-butyldimethylsilyl or trimethylsilyl; lower alkanoyl, such as acetyl; benzoyl; lower alkoxycarbonyl, such as tertutoxycarbonyl; tetrahydropyranyl; phenyl-lower alkoxycarbonyl, such as benzyloxycarbonyl; and unsubstituted or substituted 1-phenyl-lower alkyl, such as benzyl or p-methoxybenzyl.

The protecting groups may be present in any precursors and intermediates and should protect the functional groups concerned against unwanted secondary reactions, such as acylations, etherifications, esterifications, oxidations, solvolysis, and similar reactions. In certain cases, the protecting groups may, in addition to this protection, effect a selective, typically stereoselective, course of reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/1, Georg Thieme Vedag, Stuttgart 1974, in H.-D. Jakubke and H. Jescheit, "Aminosäuren, Peptide, Proteine" (*Amino adds, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

The prefix "lower" means that the respective moiety preferably has up to and including a maximum of 7 carbon atoms, more preferably up to 4 carbon atoms.

Lower alkyl can be linear or branched and is especially methyl, ethyl, n-propyl, isopropyl, n-butyl, isobutyl, sec-butyl or tert-butyl.

Halogen is preferably fluorine, chlorine, bromine or iodine.

Any reference to other documents or publications within this application means that the respective document or publication is included by reference into the present disclosure.

The process steps making up the process of the invention and the preferred aspects thereof can be described preferably as follows:

Hereinbefore and hereinafter, the definitions of the moieties R, $X_1$, $X_2$, $X_3$ and $X_4$ have the meaning given under formula I, if not indicated otherwise. A moiety X, where mentioned, stands for a protecting group as defined above (and may, depending on the exact position, correspond to any of $X_1$, $X_2$, $X_3$ and $X_4$ if appropriate).

The reaction sequence starts with a compound of the formula II

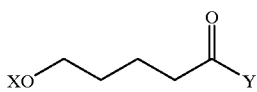

(II)

wherein Y is the radical of an organic or inorganic acid devoid of its dissociable hydrogen, e.g. halogen, especially chlorine, and X is a protecting group as described above, especially benzyl; which is reacted with an oxazolidone of the formula III

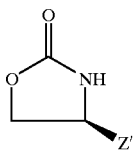

(III)

wherein Z' is lower alkyl, e.g. isopropyl, or preferably phenyl-lower alkyl, especially benzyl, in an appropriate solvent, e.g. tetrahydrofuran, in the presence of a strong base, especially methyl magnesium bromide, and then of an appropriate tertiary amino base, such as 4-dimethylaminopyridine; or preferably of an alkalimetal alkylid, such as n-butyl-lithium; at low temperatures, e.g. in the range from −80 to +10° C., yielding a compound of the formula IV,

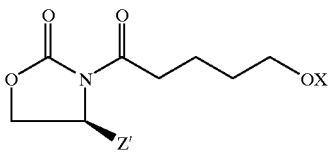

(IV)

wherein X and Z' have the meanings given above; (IV) is then C-methlyated, e.g. with a halomethane, especially methyliodide, in the presence of a strong base, e.g. sodium hexamethyldisilazide, to yield a compound of the formula V,

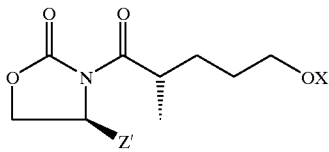

(V)

wherein X and Z' are defined as above; from that compound, then a compound of the formula VI,

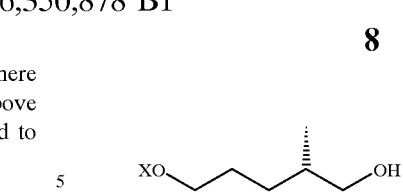

(VI)

wherein X is as given above is set free by reductive cleavage, e.g. by reaction with a complex hydride, such as lithium aluminium hydride; then, a protecting group X' selected from the protecting groups mentioned above for $X_1$ to $X_4$, but different from X in formula VI, preferably tert-butyl-dimethylsilyl, is introduced at the free hydroxy group that allows that the protecting group X in the compound of formula VI can be cleaved off without affecting the newly introduced protecting group, e.g. by reaction with an alkylsilylhalogenide, such as tert-butyldimethylsilyl chloride, to yield a bis-protected compound of the formula VII,

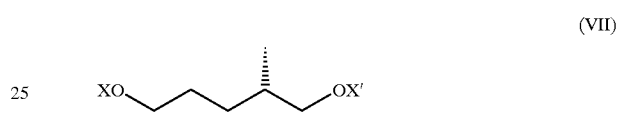

(VII)

with X and X' as described above; from this compound, then the protecting group X, preferably benzyl, is cleaved off under appropriate conditions, e.g. by catalytic transfer hydrogenolysis, reaction with lithium 4,4'-di-tert-butyl-biphenyl or by catalytic hydrogenation, to yield a compound of the formula VIII,

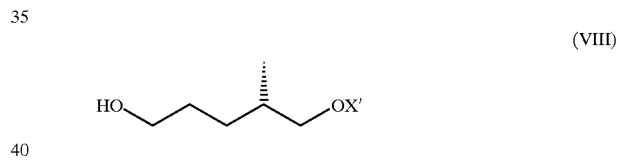

(VIII)

with X' as defined for the compound of the formula VII; that compound VIII is then reacted with a halogenide of an organic sulfonic acid to yield the corresponding sulfonic acid ester of the formula IX,

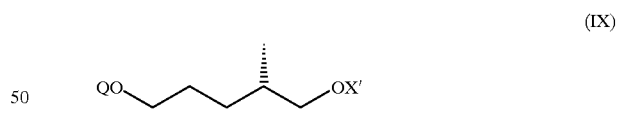

(IX)

wherein Q is organic sulfonyl, especially alkanesulfonyl, such as methanesulfonyl, and that sulfonyl ester is then reacted with a metal iodide, especially sodium iodide, to yield the corresponding iodide compound of the formula X,

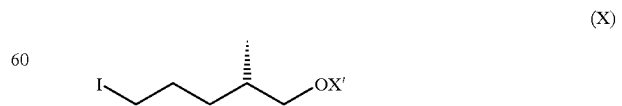

(X)

with X' as defined above.

This is the synthesis of one of the three intermediates for the convergent synthesis.

Independently from that sequence of reactions, a) a compound of the formula XI,

(XI)

wherein R is as described under formula I and Hal is halogen, especially chlorine, is reacted with a tri-alkyl phosphite, especially triethyl phosphite, to yield a phosphonate compound of the formula XII,

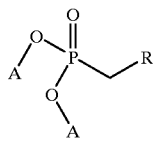
(XII)

wherein R is as defined under formula I and each of A is alkyl, especially ethyl.

Independently, (5S)-(2,2-cyclohexylidene-)-4-oxo-1,3-dioxolane (synthesized starting from L-(−)-malic acid, see Hanessian et al., J. Orgn. Chem. 58, 7768–81 (1993)) is reacted with $BH_3$-$Me_2S$ complex=dimethylsulfide BH3× Me2S ist verzichtbarto yield 3(S)-dihydro-3-hydroxy-2 (3H)-furanone (compound 11 in reaction scheme 2 below); that is then protected by introduction of a protecting group $X_4$, especially using a lower alkylsilyl halogenide, such as tert-butyldimethylsilylchloride, to yield a compound of the formula XIII,

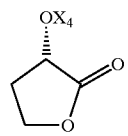
(XIII)

wherein $X_4$ is a protecting group, especially tert-butyldimethylsilyl; the compound of formula XIII is then reacted with an methyl metal or methyl metal derivative, especially methyl lithium, to the novel compound of the formula XIV,

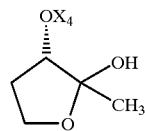
(XIV)

wherein $X_4$ is as defined under formula XIII; the compound of formula XIV is reacted with a further reagent capable of introducing a protecting group, especially an alkylsilyl halogenide, such as tert-butyldimethylsilyl chloride, yielding a compound of the formula XV,

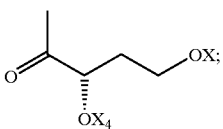
(XV)

wherein X and $X_4$ are a protecting group, especially tert-butyldimethylsilyl, which compound is then reacted with a phosphonate compound of the formula XII given above in the presence of a strong base, especially n-butyl lithium, yielding a compound of the formula XVII,

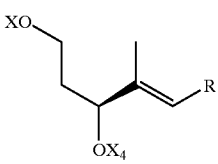
(XVII)

wherein X and $X_4$ are as defined under formula XIII and R is as defined under formula I; the compound of the formula XVII is then deprotected partially under appropriate conditions (e.g., if X is tert-butyldimethylsilyl, by using aqueous hydrofluoric acid) to give a compound of the formula XVIII,

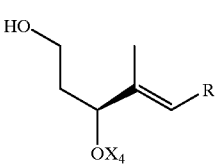
XVIII wherein the moieties $X_4$ and R are as defined under formula XVII; the compound of the formula XVIII is oxidized selectively, e.g. using dimethylsulfoxide and oxalylchloride in dichloromethane, to the corresponding aldehyde of the formula XIX,

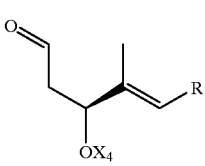
(XIX)

wherein R and $X_4$ are as defined under formula XVII, which is then, by reaction with a strong base, especially n-butyl lithium, and iodine in the presence of triphenylphosphonium iodide (either with isolation of the iodoethyl phosphonium iodide or in a one pot synthesis), and subsequent addition of a different or the same base as above, especially sodium hexamethyidisilazide, converted into a compound of the formula XX,

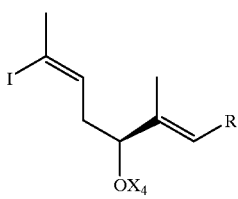

(XX)

(this reaction being highly specific in yielding mainly or purely the cis-compound wherein R and $X_4$ are as defined under formula XVII.

This reaction sequence is allowing for the introduction of a large variety of heterocyclic moieties R and thus providing an important new way of synthesizing analogs of epothilone B and desoxyepothilone B wherein R has one of the other meanings than 2-methyfthiazolyl given above under formula (I)

The sequence of reactions from XIII to XV, especially the reaction from XIII to XIV and the reaction from XIV to XV, as well as the whole sequence leading from L-malic acid to XX (as described in the examples), are new and form a special part of the invention.

The compounds of the formulae XIV (especially compound 13 in scheme 2), XVII (if R is other than 2-methylthiazol-4-yl and $X_4$ is other than tert-butyldimethylsilyl) (especially 15 in scheme 2), XVIII (if R is other than 2-methylthiazol-4-yl and $X_4$ is other than tert-buityldimethylsilyl) (especially 16 in scheme 2), the compound of formula XX if R is other than 2-methylthiazol-4-yl, and compound 18 in scheme 2, are new and are also part of the invention.

The compound of the formula XX is the second of the three intermediates for the convergent synthesis.

The third intermediate for the convergent synthesis is manufactured preferably by one of the two ways (a) and (b) described hereinafter:

(a) (see also scheme 4) Diethylketon is reacted in the presence of zinc dust (activated, e.g. with 1,2-dibromoethane) in the presence of $B(OCH_3)_3$ with ethyl 2-bromo-2-methylpropanoate (Fluka, Buchs, Schweiz) to ethyl 2,2-dimethyl-3-ethyl-3-hydroxypentanoate 22, which is then reacted with a dehydrating agent, especially phosphorus pentoxide, to ethyl (E)-2,2-dimethyl-2-ethyl-3-pentenoate 23; which is then reacted in the presence of an appropriate complex hyd fide, e.g. lithium aluminium hydride, to E-2, 2-dimethyl-3-ethyl-3-penten-1-ol 24; this is then oxidised with an appropriate oxidant, e.g. dimethylsulfoxide in dichloromethane and oxalyl chloride, to (E)-2,2-dimethyl-3-ethyl-3-pentenal 25, which is then reacted with (S)-(–)-2-hydroxy-1,2,2-triphenyl acetate (FLUKA) in the presence of a strong base, e.g. Li-di-isopropylamide, to (1S)-2,2,1-triphenyl-2-hydroxyethyl-(3S,E)-4,4-dimethyl-5-ethyl-3-hydro-xy-5-heptenoate 26; that compound is transformed, by reaction with an appropriate complex hydride, e.g. lithium aluminium hydride, into (S)-(E)-4,4-dimethyl-5-ethyl-5-heptene-1,3-diol 28, which is then converted, by reaction with acetone in the presence of anhydrous copper sulfate, a strong organic acid, e.g. p-toluene sulfonic acid, and a tertiarry nitrogen base, e.g. pyridine, to give (S)-(E)-2,2-dimethyl-[1,3] dioxan-4-yl)-3-ethyl-2-methyl-pent-3-ene 29; this compound is then converted to the third intermediate for the convergent synthesis, the ethyl ketone (S)-2-(2, 2-dimethyl-[1,3]dioxan-4-yl)-2-methyl-pentan-3-one 30 by ozonolysis.

(b) (see scheme 3) Alternatively, 30 can be obtained advantageously by reaction of (2R)-N-acetylbo mane-10,2-sultam (see Tetrahedron Lett. 33, 2439 (1992)) in the presence of a dialkylborane triflate or dialkylborane chloride, especially diethylborane triflate (which can, but does not have to be, generated in situ from triethylborane and $CF_3SO_3H$) and after addition of a tertiary nitrogen base, e.g. diisopropylethyl amine, with 2,2-dimethyl-3oxo-pentanal (see J. Am. Chem. Soc. 119, 7974 (1997)) that leads to the sultam product 31, which is then reacted, in the presence of a tertiary nitrogen base, such as 2,6-lutidine, with a reagent appropriate for the introduction of a protecting group, e.g. an alkylsilylhalogenide, especially tert-butyldimethylsilyl-triflate, to give a compound of the formula XXI

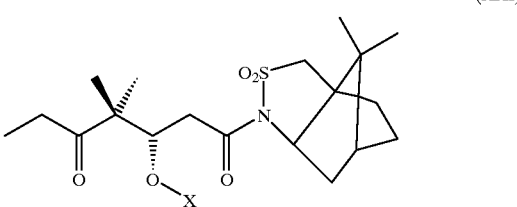

(XXI)

wherein X is a protecting group, especially tert-butyldimethylsilyl (especially compound 32); the compound of formula XXI is then converted into the corresponding free acid of the formula XXII by reaction with an appropriate aqueous base, e.g. LiOH, NaOH, KOH, or LiOOH, especially with LiOOH

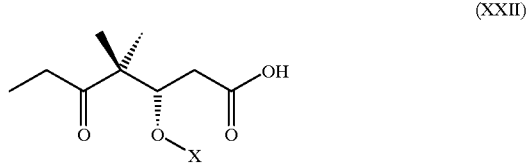

(XXII)

wherein X is as defined under formula XXI (especially compound 33); the compound of formula XXII is then reduced to the corresponding alcohol of the formula XXIII

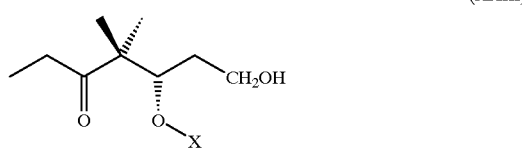

(XXIII)

wherein X is as defined under formula XXI (especially compound 34), by reaction eg. with Borane/dimethylsulfide, and finally that compound is deprotected and transformed into compound 30 by reaction in acetone/acid, such as acetoneltrifluoroacetic acid.

Thus, the third intermediate for the convergent synthesis of the compound of the formula I is prepared.

In a next step, first the two intermediates of the formulae X and XX (preferably compounds 8 and 18 in scheme 5) are coupled by reaction of the compound of the formula X with a suspension of powdered Zn/Cu couple in the presence of an activator, e.g. 1,2-dibromoethane, in the presence of halotrialkylsilane, such as chlorotrimethylsilane (i necessary with addition of trifluoromethanesulfonate and catalytic amounts of mercury(II) acetate to complete the first part of the reaction, and then addition of XX and a Pd(O)-complex yielding a compound of the formula XXIV,

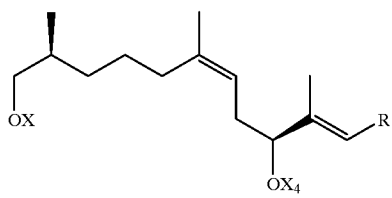

(XXIV)

wherein X and $X_4$ each are a protecting group, especially tert-butyldimethylsilyl, and R is as defined under formula I; the advantage of this coupling is that it yields the cis-isomer of the compound of the formula XXIV in high yield and stereospecificity the compound of the formula XIV is then selectively deprotected, e.g. (in the case of X=alkylsilyl, especially tertbutyl-dimethylsilyl) by campher sulfonic acid, to give a compound of the formula XXV,

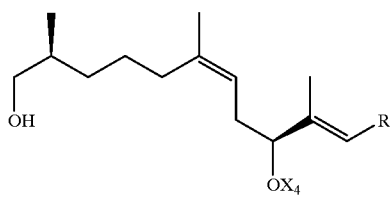

(XXV)

wherein $X_4$ and R are as defined under formula XXIV; the compound of the formula XXV is then oxidized with an appropriate oxidant, e.g. Dess-Martin periodinane, to the corresponding aldehyde of the formula XXVI

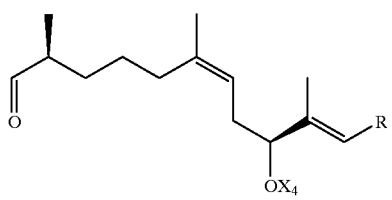

(XXVI)

wherein $X_4$ and R are as defined under formula XXIV.

The compounds of the formulae XXIV and XXV in essentially isomeric pure cis-form, especially if R is other than 2-methylthiazolyl) are new and also part of the invention, as well as the coupling reaction of the compounds of the formulae X and XX to the compound of the formula XXIV.

The third intermediate of the convergent synthesis, compound 30, is then reacted with the compound of the formula XXVI (preferably compound 21) in an Aldol reaction, preferably by reaction in the presence of lithium diisopropylamide (LDA) that is first reacted with compound 30, followed by addition of the compound of the formula XXVI, resulting in a compound of the formula XXVII,

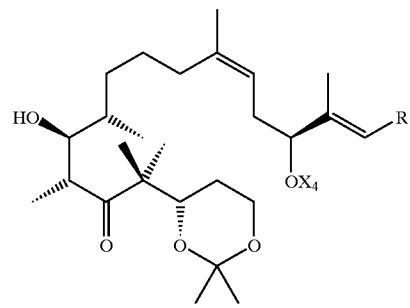

(XXVII)

wherein $X_4$ and R are as defined under formula I; the compound of the formula XXVII is then deprotected under removal of the acetal moiety, e.g. using pyridinium-p-toluenesulfonate, yielding a compound of the formula XXVIII,

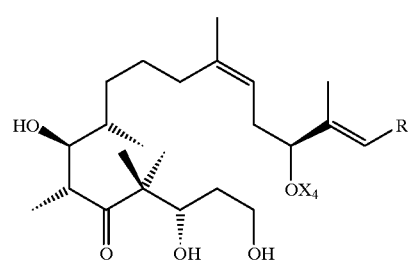

(XXVIII)

wherein $X_4$ and R are as defined under formula I; finally, the compound of the formula I is obtained by introduction of protecting groups $X_1$, $X_2$ and $X_3$ with appropriate reagents, e.g. alkylsilyl halogenides or alkylsilyl trifluoromethanesulfonates, especially tert-butyl-dimethylsilyltrifluoromethanesulfonate, in the presence of an appropriate tertiary nitrogen base, such as 2,6-lutidine.

The compound of the formula XXIV, especially where R is other than 2-methylthiazol-4-yl, is also part of the invention.

All reactions are done in appropriate solvents, at appropriate temperatures and, if necessary, under an inert gas, such as argon or nitrogen.

The invention relates also to any novel intermediates and to any novel ways of synthesis of such intermediates, as well as to novel single reaction steps, especially those leading to such novel intermediates, and combinations of such reaction steps.

The skilled person will understand that the reaction conditions given above can be replaced by analogous reaction conditions that are in principle known in the art. In addition, the skilled person will be able to select the appropriate specific reaction conditions for the reaction steps given hereinbelow and hereinafter where reactions are described generally herein. All those reaction conditions are included in the scope of the present invention.

The reactions given above are preferably carried out under conditions analogous to those given in the Examples.

The invention relates most especially to the above reaction sequences where the respective intermediates and educts mentioned in the examples are used instead of the general formulae II to presented above.

The starting materials are known, can be synthesized according to known procedures, are available commercially or can be synthesized in analogy to the materials given below in the examples.

EXAMPLES

The following examples are intended to illustrate the invention without being intended to mean any restriction of the scope of the invention:

Temperatures are given in degrees Celsius (° C.). The abbreviations used have the following meanings:

| | |
|---|---|
| h | hour(s) |
| min | minute(s) |
| m.p. | melting point |
| MW | molecular weight |
| MS | Mass Spectroscopy |
| NaHMDS | sodium hexamethyldisialazide |
| NMR | Nuclear Magnetic Resonance |
| OTBDMS | tert-butyl-dimethylsilyloxy |
| Pd(PPh$_3$)$_4$ | Palladium-tetrakis-(triphenylphosphin) |
| PPTS | pyridinium-p-toluenesulfonate |
| r.t. | room temperature |
| TBDMSO | tert-butyl-dimethylsilyloxy |
| THF | tetrahydrofurane |
| tlc | thin layer chromatography (Polygram SIL G/UV, Macherey & Nagel, Duren, FRG) |

Where physical data are not provided, the respecctive compound is used directly in the subsequent reaction step.

Flash chromatography is performed on silica gel columns (Kieselgel 60 (0.035–0.07 mm), Fluka, Buchs, Schweiz)

1) "C5" fragment (Scheme 1)

a) 5-Benzyloxyoentanoyl Chloride 1

Oxalyl chloride (1.49 ml, 17.06 mmol, 1.5 equiv) is added dropwise under nitrogen atmosphere to a solution of 2,368 g (11.37 mmol) 5-benzyloxypentanoic acid [L. Börjesson et al., J. Org. Chem. 60, 2989–2999 (1995)] in 15 ml of CH$_2$Cl$_2$. The mixture is stirred for 90 min at r.t. and 15 min at 40° C. Removal of the solvent in vacuo gives 2.425 g (94%) of 5-benzyl-oxypentanoyl chloride 1 as a colourless oil. $^{13}$C-NMR (100 MHz, CDCl$_3$): δ=171.3; 137.4; 128.7; 128.5; 128.3; 69.4; 46.2; 29.8; 22.3; 19.1 b) (S)-3-(5-Benzyloxy-1-oxopentyl)-4-(methylethyl)-2-oxazolidinone 2a (Z=isopropyl in Scheme 1)

9,6 ml (28.8 mmol, 1.2 eq) of a solution of methyl magnesium bromide (3.0 M in THF) are added dropwise to a solution of (S)-4-methylethyl-2-oxazolidinone (3.100 g, 24.0 mmol) in THF (60 ml) at 0° C. within 15 min. The mixture is stirred for 15 min at 0° C. 4-Dimethylaminopyridine (59 mg, 0.48 mmol, 0.02 equiv) is added and the mixture is cooled to −78° C. A solution of of 5-benzyl-oxypentanoyl chloride 1 (6,625 g, 29.22 mmol, 1.22 eq) in THF (20 ml) is added slowly within 30 min. The mixture is stirred for 15 min at −78° C. and then for 30 min at 0° C. Saturated aqueous NH$_4$Cl solution (40 ml) is added with stirring. The organic phase is separated and the aqueous layer is extracted with diethyl ether (3×100 ml). The combined organic extracts are dried over magnesium sulfate and concentrated in vacuo. Purification of the residue by flash column chromatography (pentane/diethyl ether 2:1) affords (S)-3-(5-benzyioxy-1-oxopentyl)4-(methylethyl)-2-oxazolidinone 2 (5.602 g, 73%) as a colourless oil which crystallizes upon standing in the cold. Recrystallization from pentane/diethyl ether yields colourless crystals, m.p. 133° C. $^{13}$C-NMR (100 MHz, CDCl$_3$): δ=173.0; 154.0; 138.5; 128.3; 127.6; 127.4; 72.8; 69.9; 63.3; 58.3; 35.2; 29.0; 28.3; 21.1; 17.9; 14.6 c) 3-(5-Benzyloxy-2S-methyl-1-oxopentyl)-4S-(methylethyl)-2-oxazolidinone 3a (Z=isopropyl in Scheme 1)

To 10.1 ml (10.1 mmol, 1.1 equiv) of a solution of sodium hexamethyldisilazide (NaHMDS, 1.0 M in THF) is added a solution of (S)-3-(5-benzyloxy-1-oxopentyl)-4-(methylethyl)-2-oxazolidinone 2 (2,928 g, 9.17 mmol) in 10 ml of THF dropwise at −78° C. The mixture is stirred for 1 h at −78° C. A solution of iodomethane (2.9 ml) in 12.0 ml of THF is added dropwise. The mixture is stirred for 8 h at −78° C. Saturated aqueous NH$_4$Cl solution (40 ml) is added with stirring. The organic phase is separated and the aqueous layer is extracted with diethyl ether (3×100 ml). The combined organic extracts are dried over magnesium suffate and concentrated in vacuo. Purification of the residue (ratio of the diastereomeric alkylation products about 10:1) by flash column chromatography (pentane/diethyl ether 2:1) affords 3-(5-benzyloxy-2S-methyl-1-oxopentyl)-4S-(methylethyl)-2-oxazolidinone 3 (2.142 g, 70%) as a colourless oil (3:1 mixture of 3a and its 2R diastereomer). $^{13}$C-NMR (100 MHz, CDCl$_3$): δ=176.9; 153.6; 138.5; 128.3; 127.5; 127.4; 72.8; 70.2; 63.1; 58.4; 37.5; 29.7; 28.4; 27.4; 18.0; 17.9; 14.6 d (S)-5-Benzyloxy-2-methyl-pentan-1-ol 4

Lithium aluminium hydride (235 mg, 6.19 mmol, 1.0 equiv) is added portionwise within 45 min at 0° C. to a solution of 2.064 g (6.19 mmol) of 3-(5-benzyloxy-2S-methyl-1-oxopentyl)-4S-(methylethyl)-2-oxazolidinone 3 in 35 ml of absolute diethyl ether. The mixture is stirred at 0° C. for 15 min and analyzed by tic. If starting material can still be detected, lithium aluminium hydride addition is continued until completion of the reaction. 235 μl of water, 235 μl of aqueous sodium hydroxide solution (15%) and 610 μl of water are subsequently added to the reaction mixture (or the volumes corresponding to the amount of lithium aluminium hydride added, respectively). The mixture is stirred until the precipitation of a white solid is complete and filtered through a small plug of celite. The filtrate is concentrated in vacuo. Purification of the residue by flash column chromatography (pentane/diethyl ether 1:1) affords (S)-5-benzyloxy-2-methyl-pentan-1-ol 4 (1.160 g, 90%) as a colourless oil. $^{13}$C-NMR (100 MHz, CDCl$_3$): δ=138.5; 128.3: 127.6; 127.5; 72.9; 70.6; 68.1; 35.5; 29.5; 27.1; 16.5

[Alternatively (using Z=benzyl in reaction scheme 1), 4 can be synthesized as follows:

b*) 4(S)-(Benzyl)-3-(5-benzyloxy-1-oxopentyl)-2-oxazolidinone 2a (Z=isopropyl in Scheme 1)

To a solution of 2.03 g of 4-(S)-benzyl-oxazolidin-2-one in 30 ml of THF, 7.23 ml of a 1.6 M solution of n-BuLi in hexane at −78° are added over a period of 10 min. To this solution then 2.86 g of 5-benzyloxypentanoyl chloride 1 are added at the same temperature and the mixture is stirred at −78° for 30 min. After that time the reaction is quenched by the addition of 10 ml of saturated aqueous NH$_4$Cl, the THF is removed by evaporation, the residue is diluted with dichloromethane/water and the organic layer is separated off. The aqueous solution is extracted three times with 30 ml of dichloromethane, respectively, and the combined organic extracts are washed with 50 ml of 1N NaOH (once) and 50 ml of brine (once). After drying over MgSO$_4$ and evaporation of solvent the residue is purified by FC in hexane/ether 1/1 to give 3.76 g of 2b as an oil. $^1$H-NMR (CDCl$_3$): δ=7.35–7.15 m (10H); 4.65 m (1H); 4.5 s (2H); 4.15 d (2H); 3.5 t (2H); 3.25 dd (1H); 3.25 dd (1H); 2.95 m (2H); 2.7 dd (1H); 1.90–1.45 m (4H).

c*) 4S-(Benzyl)-3-(5-benzyloxy-2S-methyl-1-oxopentyl)-2-oxazolidinone 3b (Z=benzyl in Scheme 1)

All non-aqueous steps are carried out under argon. A solution of 205 g of compound 2b in 800 ml of THF is added dropwise at −75° to 690 ml of a 1 M solution of NaHMDS in THF. After completion of the addition (ca. 2h), the solution is stirred for an additional 30 min at −70° after which time a solution of 198 ml of methyl iodide in 800 ml of THF is added dropwise at the same temperature (ca. 45 min). The mixture is then stirred at −70° for 75 min, the cooling bath is removed and the mixture is allowed to warm to room temperature. After addition of 300 ml of THF/water 1/1 followed by 250 ml of saturated aqueous $NH_4Cl$ the organic layer is separated and the remaining aqueous solution is extracted three times with 300 ml of t-butyl-methyl ether each. The combined organic extracts are evaporated to dryness and the residue is purified by FC in t-butyl-methyl etherlhexane 1/1 to yield a ca. 11/1 mixture of diastereoisomers. Recrystallization of this material from ethyl acetatel hexane (ca. 1/10) gave 98.5 g of 3a, which was diastereomerically pure. M.p. 51.5–53.3° C. $^1$H-NMR ($CDCl_3$): δ=7.5–7.15 m (10H); 4.65 m (1H); 4.45 s (2H); 4.1 m (2H); 3.75 m (1H); 3.45 m (2H); 3.25 dd (1H); 2.75 dd (1H); 1.90–1.45 m (4H); 1.20 d (3H).

d*) (S)-5-Benzyloxy-2-methyl-pentan-1-ol 4:

150 ml of a 1M solution of $LiAlH_4$ in THF at 5° are added over a period of 20 min to a solution of 67.5 g of compound 3b in 700 ml of dry THF are added. The reaction mixture is stirred at room temperature for 1 h and then quenched by addition of 17 ml of THFlwater 10/7 followed by 6.5 ml of 4N NaOH and 15 ml of water. The resulting precipitate is removed by filtration, the residue washed with 250 ml of THF and the filtrate is evaporated. The residue is then redissolved in 250 ml of ethyl acetate and this solution extracted with 200 ml each of water, 1N NaOH, water, 1N HCl, and water followed by 300 ml of brine. The solvent is evaporated and the residue is three times co-evaporated with 100 ml of toluene. Vacuum distillation of the residue at 0.69 Torr gave 26 g of 4a as a colouriess oil (b.p. 105°). MS ($C_{13}H_{20}O_2$; 208.3): 209 [M+H]. $^1$H-NMR ($CDCl_3$): δ=7.35–7.25 m (5H); 4.5 s (2H); 3.45 m (4H); 1.8–1.4 m (3H); 1.2 m (1H); 0.95 d (3H).]

Further process after any of the 2 variants for synthesis of compound 4:

e) (S)-1-Benzyloxy-5-tert-butyldimethylsilyloxy)-4-methyl-pentane 5

Imidazole (1.230 g, 18.06 mmol, 2.6 equiv) and tert-butyl-dimethylsilyl chloride (1.230 g, 9.03 mmol, 1.3 equiv) are added to a solution of (S)-5-benzyloxy-2-methyl-pentan-1-ol- 4 (1.447 g, 6.95 mmol) in dimethyl formamide (5.5 ml). The mixture is stirred for 1 h at 40° C. Purification of the reaction mixture by flash column chromatography (pentane/diethyl ether 20:1) affords (s)-1-benzyloxy-5-(tert-butyldimethylsilyloxy)-4-methyl-pentane 5 (1.985 g, 89%) as a colouriess oil (the reaction mixture is poured directly without aqueous workup onto a flash chromatography column which is pre-wetted with the eluent). $^{13}$C-NMR (100 MHz, $CDCl_3$): δ=138.7; 128.3; 127.5; 127.4; 72.8; 70.8; 68.2; 35.6; 29.6; 27.2; 25.9; 18.3; 16.6; −5.4.

f) (S)-5-(tert-Butyidimethylsilyloxy)-4-methyl-pentan-1-ol 6

Three variants (i), (ii) or (iii) are possible:

(i) Catalytic Transfer Hydrogenolysis Protocol: 48.5 mg of $Pd(OH)_2$ on activated charcoal (20%) (Pearlman's catalyst) is added to a solution of (S)-1-benzyloxy-5-(tert-butyldimethylsilyloxy)-4-methyl-pentane 5 (485 mg, 1.5 mmol) in 12.0 ml of absolute ethanol and 6.0 ml of cyclohexene. The mixture is heated under ref lux until the reaction is completed (tlc monitoring). If starting material can still be detected after 8 h, some catalyst is added and refluxing is continued until the reaction is completed. After cooling to room temperature the catalyst is filtered off. The filtrate is concentrated in vacuo. Purification of the residue by flash column chromatography (pentane/diethyl ether 5:1) affords (S)-5-(tert-butyldimethylsilyloxy)4-methyl-pentan-1-ol 6 (565 mg, 97%) as a colourless oil.

(ii) Debenzylation with Lithium 4,4'-di-tert-butyl-biphenyl (LiDTBBP):

Preparation of LiDTBBP solution: With stirring, 4,4'-di-tert-butyl biphenyl (3.6 g) under an Argon atmosphere is added at 0° C. to a suspension of lithium (30% in mineral oil) in THF (30 ml). Stirring is continued for 2 h at r.t. The resulting deep green solution is added dropwise to a solution of (S)-1-benzyloxy-5-(ter-butyldimethylsilyloxy)-4-methyl-pentane 5 (673 mg, 2.09 mmol) in 10 ml of THF at −78° C., until the colour of the mixture remains green (or until tic analysis shows completion of the reaction, respectively). Saturated aqueous $NH_4Cl$ solution (10 ml) is added with stirring. The organic phase is separated and the aqueous layer is extracted with diethyl ether (3×50 ml). The combined organic extracts are dried over magnesium sulfate and concentrated in vacuo. Purification of the residue by flash column chromatography (pentane/diethyl ether 5:1) affords (S)-5-(tert-butyldimethylsilyloxy)-4-methyl-pentan-1-ol 6(471 mg, 97%) as a colourless oil. $^{13}$C-NMR (100 MHz, $CDCl_3$): δ=68.29; 63.36; 35.57; 30.24; 29.25; 25.98; 18.38; 16.77; −5.34

(iii) Catalytic hydrogenation: 102 g of compound 5 in 1800 ml of ethanovcyclohexane 2/1 are hydrogenated over 10% Pd-C (10 g) at room temperature and atmospheric pressure for 16h. After removal of the catalyst by filtraton the solvents are evaporated and the residue is purified by silica gel chromatography in hexane/ethyl acetate 6/1→1/1 to yield 72 of 6.

g) (S)-1-Methanesulfonyloxy-5-(tert-butyldimethylsilyloxy)-4-methyl-pentane 7

Triethyl amine (413 μl, 3.09 mmol, 1.53 equiv) and methanesulfonyl chloride (212 μl, 2.73 mmol, 1.35 equiv) is added to a solution of (S)-5-(tert-butyldimethylsilyloxy)-4-methyl-pentan-1-ol 6 (471 mg, 2.03 mmol) in 6.5 ml of dichloromethane. The mixture is stirred for 15 min at 0° C., diluted with diethyl ether (30 ml), washed with water (5 ml), 1.0 M hydrochloric acid (5 ml), saturated aqueous sodium bicarbonate solution (5 ml), and brine (5 ml). The organic phase is separated, dried over magnesium sulfate and concentrated in vacuo. (S)-1-methanesudonyloxy-5-(tert-butyldimethylsilyloxy)-4-methyl-pentane 7 (472 mg, 99%) is obtained as a colourless oil. $^{13}$C-NMR (100 MHz, $CDCl_3$): δ=70.44; 67.98; 37.41; 35.31; 28.99; 26.80; 25.95; 18.34; 16.56; −5.37, −5.38 (—$SiMe_2tBu$).

Scheme 1

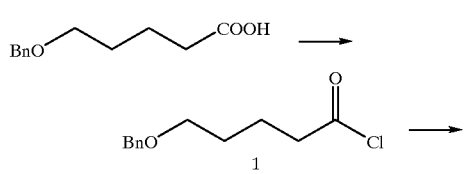

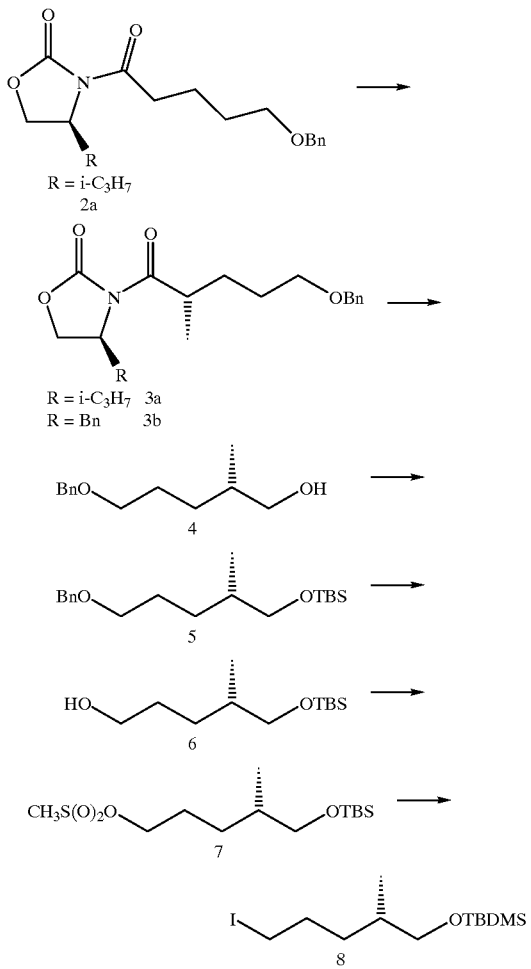

h) (S)-1-Iodo-5-(tert-butyldimethylsilyloxy)-4-methyl-pentane 8

Anhydrous sodium iodide (600 mg, 4.0 mmol, 2 equiv) is added to a solution of (S)-1-methanesulfonyloxy-5-(tert-butyldimethylsilyloxy)-4-methyl-pentane 7 (622 mg, 2.0 mmol) in 3.0 ml of absolute acetone. The mixture is stirred for 2 h at 50° C. 10 ml of a mixture of brine and water (1:1) are added, and the mixture is extracted with diethyl ether (3×20 ml). The combined organic extracts are dried over magnesium sulfate and concentrated in vacuo. Purification of the residue by flash column chromatography (pentane/diethyl ether 20:1) affords (S)-1-iodo-5-(tert-butyidimethylsilyloxy)-4-methyl-pentane 8 (647 mg, 94%) as a colourless oil. FG 342.34; $^{13}$C-NMR (100 MHz, CDCl$_3$): δ=68.1, 35.1, 34.3, 31.3, 26.0, 16.7, 7.4, −5.3

2) The Thiazole Seament (Scheme 2)

a) 4-Chloromethyl-2-methylthiazole 9

A solution of thioacetamide (3.757 g, 50 mmol) is added dropwise to a saturated solution of 1,3-dichloroacetone (6.683 g, 50 mmol) in acetone. After a few minutes, a crystalline solid precipitates (the reaction can be initiated or accelerated by immersion of the reaction flask into an ultrasonic bath for a few seconds). In order to complete crystallisation, the reaction flask is left stand over night at r.t. The resulting suspension is filtered through a suction filter. The solid is washed with a few ml of acetone. A solution of the solid in ethanol (40 ml) is refluxed for 3 h. After the mixture is cooled to r.t. the solvent is removed in vacuo. Saturated aqueous sodium bicarbonate solution (50 ml) is added, and the mixture is extracted with diethyl ether (3×50 ml). The combined organic extracts are dried over magnesium sulfate and concentrated in vacua. 4-Chloromethyl-2-methylthiazole 9 (7.138 g, 97%) is obtained as a pale yellow oil after complete evaporation of the solvent. $^1$H-NMR (400 MHz, CDCl$_3$): δ(ppm)=7.14 (s, 1H, H-5); 4.65 (s, 2H, —CH$_2$Cl); 2.72 (s, 3H, —CH$_3$); $^{13}$C-NMR (100 MHZ, CDCl$_3$): δ(ppm)=166.9; 151.6; 116.9; 40.7; 19.1

CAUTION: The reaction is strongly exothermic and it may not immediately take place after addition of the thioacetamide is started. The onset of the reaction can be delayed to the point where all of the thioacetamide has already been added, resulting in a vigorous and uncontrolled blow-up of the reaction mixture. It is therefore advisable to add the thioacetamide at 50°. If the reaction is not initiated after addtition of 10% of the projected amount of thioacetamide the addition should be halted and only continued after onset of the reaction.

b) Diethyl-(2-methylthiazol-4-yl)-methanephosrhonate 10

A mixture of 4-chloromethyl-2-methylthiazole 9 (3.691 g, 25 mmol) and triethyl phosphite (6.64 ml, 50 mmol) is stirred for 6 h at 160° C. Excess triethyl phosphite is distilled off under oil pump vacuum (4 mm). Purification of the residue by flash column chromatography (methanol/diethyl ether 19:1) yields diethyl-(2-methylthiazol-4-yl)-methanephosphonate 10 (5.066 g, 82%) as a colourless oil. Alternatively, the product can be isolated by high vacuum distillation (b.p. 110° C./0.25 mm) together with some starting material 9 (b.p. 70° C./2 mm). $^{13}$C-NMR (CDCl$_3$) δ=164.3; 153.1; 142.2; 131.4; 125.7; 118.8; 114.9; 78.7; 68.3; 35.7; 34.6; 32.9; 27.8; 27.1; 25.9; 19.2; 18.3; 18.2; 16.7; 13.9; −4.7; 4.9; −5.4.

c) (3S)-Dihydro-3-hydroxy-2(3H)-furanone [(S)-2-Hydroxy-γ-butyrolactone] 11

Dropwise via syringe, a solution of (5S)-(2,2-cyclohexylidene-4-oxo-1,3-dioxolan-5-yl)acetic acid [synthesized starting from L-(−) malic acid, see S. Hanessian et al., J. Org. Chem. 58, 7768–7781 (1993)] (15.04 g, 70.2 mmol) in 70 ml of dry THF is aded to a mixture of 2.0 M BH$_3$-DMS complex (100 ml, 200.0 mmol) and B(OCH$_3$)$_3$ (24.2 ml, 200.0 mmol) in 175 ml of dry THF cooled at 0° C. The reaction mixture is stirred over night at room temperature and cooled to 0° C., and 70 ml of MeOH is added dropwise via syringe. The mixture is stirred for 1 h, and the solvent is removed under reduced pressure to afford a thick oil. This process is repeated twice with MeOH (105 ml) to afford a colourless oil. The crude product (a mixture of 11 and (5S)-(2-Hydroxyethyl)-2,2-cyclohexylidene-1,3-dioxolan-4-one) is dissolved in 175 ml of dichloromethane. p-Toluenesulfonic acid is added (1.335 g, 7.02 mmol, 0.1 eq) and the mixture is stirred for 24 h at r.t. Triethyl amine (980 μl) is added and the mixture is concentrated in vacuo. Purification of the residue by flash column chromatography (diethyl ether) affords (3S)-dihydro-3-hydroxy-2(3H)-furanone 11 (5.160 g, 72%) as a colourless oil. $^{13}$C-NMR (100 MHz, CDCl$_3$): δ(ppm)=178.2; 67.4; 65.2; 30.8 d) (S)-2-(tert-Butyldimethylsilyloxy)-g-butyrolactone 12

Imidazole (241 mg, 3.54 mmol, 2.2 equiv) and tert-butyl-dimethylsilyl chloride (267 mg, 1.77 mmol, 1.1 equiv) are added to a solution of (3S)-dihydro-3-hydroxy-2(3H)-furanone 11 (164 mg, 1.61 mmol) in dimethyl formamide (1.5 ml). The mixture is stirred for 24 h at r.t. Purification of the reaction mixture by flash column chromatography (pentane/diethyl ether 10:1) affords (S)-2-(tert-butyidimethylsilyloxy)-γ-butyrolactone 12 (321 mg, 93%) as a colourless oil. $[α]_D^{20}$=−31.7; $[α]_{546}^{20}$=−37.4 (c=0.86, CHCl$_3$); $^{13}$C-NMR (100 MHz, CDCL$_3$): δ(ppm)=175.8; 68.2; 64.7; 32.3; 25.6; 18.2; −4.8; −5.3 e) (3S)-3-(tert-Butyldimethylsilyloxy)-2-hydroxy-2-methyl-tetrahydrofurane 13

Methyl lithium (670 μl [1.11 mmol, 1.1 equiv] of a 1.65 M solution in diethyl ether) is added dropwise to a stirred solution of (S)-2-(tertbutyidimethylsilyloxy)-γ-butyrolactone 12 (218 mg, 1.01 mmol) in THF (4.0 ml) cooled to −78° C. is added dropwise. After stirring at −78° C. for 3 h, the reaction is quenched by the addition of glacial acetic acid (72 μl, 1.26 mmol, 1.25 equiv). Diethyl ether (20 ml) and saturated aqueous sodium bicarbonate solution (10 ml) are added. After stirring for 5 min the organic layer is separated and the aqueous layer is extracted with diethyl ether (2×20 ml). The combined organic extracts are dried over magnesium sulfate and concentrated in vacua. Crude (3S)-3-(tertbutyidimethylsilyloxy)-2-hydroxy-2-methyl-tetrahydrofurane 13 (235 mg, 93%) is obtained as a colourless crystalline solid (mixture of diastereomers) which is used for the synthesis of (S)-3,5-di-(tert-butyldimethylsilyloxy)-pentan-2-one 14 without further purification.

f) (S)-3,5-Di-(tert-Butyldimethylsilyloxy)-pentan-2-one 14

Imidazole (125 mg, 1.84 mmol, 2.2 equiv) and tert-butyl-dimethylsilyl chloride (139 mg, 0.92 mmol, 1.1 equiv) are added to a solution of (3S)-3-(tert-butyldimethylsilyloxy)-2-hydroxy-2-methyl-tetrahydrofurane 13 (194 mg, 0.83 mmol) in dimethyl formamide (800 μl). The mixture is stirred for 24 h at r.t. Purification of the reaction mixture by flash column chromatography (pentane/diethyl ether 20:1) affords (S)-3,5-di-(tert-butyidimethylsilyloxy)pentan-2-one 14 (226 mg, 78%) as a colourless oil. $[α]_D^{20}$=−11.8; $[α]_{546}^{20}$=−14.1 (c=1.0, CHCl$_3$); $^1$H-NMR (200 MHz, CDCl$_3$): δ(ppm)=4.16 (dd, 1H); 3.8–3.5 (m, 2H); 2.16 (s, 3H); 1.9–1.7 (m, 2H); 0.92 (s, 9H); 0.88 (s, 2H); 0.06 (s, 6H); 0.04 (s, 3H), 0.03 (s, 3H)

g) (S,4E)-1,3-Di-(tert-butyldimethylsilyloxy)-4-methyl-5-(2-methylthiazol-4-yl)-pent-4-ene 15

(see D. Schinzer et al., Chem. Eur. J. 2, 1477–1482 (1996)) n-Butyl lithium (23,5 ml [58.7 mmol, 1.2 equiv] of a 2.5 M solution in hexanes) is added dropwise to a stirred solution of diethyl-(2-methylthiazol-4-yl)-methanephosphonate 10 (14,64 g, 58.7 mmol, 1.2 equiv) in THF (150 ml) cooled to −78° C. After stirring at −78° C. for 1 h, a solution of (S)-3,5-di-(tertbutyidimethylsilyloxy)-pentan-2-one 14 (16.96 g, 48,9 mmol, 1.0 equiv) in 100 ml of THF is added dropwise at −78° C. The mixture is warmed to r.t. within 12 h. The reaction is quenched with saturated aqueous ammonium chloride solution (100 ml). The organic layer is seperated and the aqueous layer is extracted with diethyl ether (3×100 ml). The combined organic extracts are dried over magnesium sulfate and concentrated in vacuo. Purification of the residue by flash column chromatography (gradient elution with pentane/dichloromethane 4:1→dichloromethane→diethyl ether→diethyl ether/methanol 10:1) affords (S,4E)-1,3di-(tert-butyldimethylsilyloxy)-4-methyl-5-(2-methylthiazol-4-yl)-pent-4-ene 15 (17,07 g, 38.6 mmol, 79%) as a colourless oil and some starting material (10 and 14). Alternatively, the crude product obtained after extraction can be directly used in the next step.

h) (S,4E)-3-(tert-Butyldimethylsilyloxy)-1-hydroxy-4-methyl-5-(2-methylthiazol-4-yl)-pent-4-ene 16 (see Schinzer et al., Chem. Eur. J. 2, 1477–82 (1996))

20 ml of aqueous hydrofluoric acid (40%) at 0° C. is added to a vigorously stirred solution of (S,4E)-1,3-di-(tert-butyldimethylsilyloxy)-4-methyl-5-(2-methylthiazol-4-yl)-pent-4-ene 15 (13.255 g, 30.0 mmol) in 120 ml of diethyl ether and 120 ml of acetonitrile. Finely ground splinters of glass (133 mg) are added and the mixture is stirred for 2 h at 0° C. and analyzed by tlc. If starting material can still be detected another portion of hydrofluoric acid (20 ml) is added and stirring is continued for 1 h. The reaction is quenched by carefully adding solid sodium bicarbonate (84.0 g, 1.0 mol) within 15 min at 0° C. After stirring for 30 min at 0° C. water is aaded until the salts dissolve (the pH is adjusted to 6–8 by further addition of sodium bicarbonate, if necessary). The mixture is extracted with dichloromethane (4×200 ml). The combined organic extracts are washed with brine (100 ml), dried over magnesium sulfate, and concentrated in vacuo. Purification of the residue by flash column chromatography (pentane/diethyl ether 4:1) affords (S,4E)-3-(tert-butyldimethylsilyloxy)-1-hydroxy-4-methyl-5-(2-methylthiazol-4-yl)-pent-4-ene 16 (8.255 g, 84%) as a viscous, colourless oil.

i) (S,4E)3-(tert-Butyldimethylsilyloxy)-4-methyl-5-(2-methylthiazol-4-yl)-pent-4-en-1-al 17

A solution of dimethyl sulfoxide (2,04 ml, 28.8 mmol, 2.4 equiv) in 6.0 ml of dichloromethane is added dropwise within 5 min to a stirred solution of oxalyl chloride (1.14 ml, 13.2 mmol, 1.1 equiv) in 30 ml of dichloromethane cooled to −78° C. The mixture is stirred for 10 min at −70° C. A solution of (S,4E)-3-(tert-butyldimethylsilyloxy)-1-hydroxy-4-methyl-5-(2-methylthiazol-4-yl)-pent-4-ene 16 (3.93 g, 12.0 mmol) in 5 ml of dichloromethane is added dropwise within 5 min. The mixture is stirred for 30 min at −70° C. The reaction is quenched by dropwise addition of triethyl amine (8.4 ml, 60.0 mmol). The mixture is warmed to r.t. within 45 min. Water (30 ml) is added and the mixture is stirred for 10 min. The organic layer is seperated and the aqueous layer is extracted with dichloromethane (3×100 ml). The combined organic extracts are dried over magnesium sulfate and concentrated in vacuo. Purification of the residue by flash column chromatography (pentane/diethyl ether 5:2) affords (S,4E)-3-(tert-butyadimethylsilyloxy)-4-methyl-5-(2-methylthiazol-4-yl)-pent-4en-1-al 17 (3.21 g, 82%) as a pale yellow oil.

j) (S,2Z,6E)-5-(tert-butyldimethylsilyloxy)-2-iodo-6-methyl-7-(2-methylthiazol-4-yl)-hepta-2.6-diene 18

Butyl lithium (5.14 ml [12.86 mmol, 1.96 equiv] of a 2.5 M solution in hexanes) is added dropwise to a stirred suspension of ethyl triphenylphosphonium iodide (13.12 mmol, 2.0 equiv) in 60 ml of THF cooled to 0° C. The resulting clear red ylide solution is added dropwise to a rapidly stirred solution of iodine (3.163 g,12.46 mmol, 1.90 equiv) in 90 ml of THF cooled to −78° C. The resulting yellow suspension is stirred vigorously for 10 min at −78° C. and for 30 min at −30 to −40° C. 11.81 ml (11.81 mmol, 1.80 equiv) of a solution of sodium hexamethyidisilazide (NaHMDS, 1.0 M in THF) is added dropwise within 10 min at −30° C. The mixture is stirred for 15 min at −30° C. A solution of (S,4E)-3-(tert-butyidimethylsilyloxy)-4-methyl-5-(2-methylthiazol-4-yl)-pent-4-en-1-al 17 (2.137 g, 6.56 mmol) in 30 ml of THF is added dropwise within 10 min. The mixture is stirred for 10 min at −30° C. and quenched with saturated aqueous ammonium chloride solution (10 ml). Pentane (150 ml) is added and the mixture is filtered to a small plug of silica. The column is eluted with 400 ml of pentane/diethyl ether (4:1). The filtrate is concentrated in vacuo. Purification of the residue by flash column chromatography (pentane/diethyl ether 10:1) affords (S,2Z,6E)-5-(tert-butyldimethylsilyloxy)-2-iodo-6-methyl-7-(2-methylthiazol-4-yl)-hepta-2,6-diene 18 (1.640 g, 54%) as a pale yellow oil. $^{13}$C-NMR (100 MHz, CDCl$_3$): δ=164.17; 152.85; 141.50; 131.89; 118.66; 115.01; 102.09; 76.45; 43.47; 33.42; 25.58; 18.98; 17.97; 13.87; −4.90, −5.23 (—SiMe$_2$tBu)

Alternatively, the iodoethyl phosphonium iodide that is formed as a precipitate in the first step of the above reaction sequence (upon addition of n-BuLi to ethyl phosphonium iodide) can be isolated by filtration and recrystallized from dichloromethane/THF. It is an air-stable crystalline yellow solid (m.p.; $^1$H-NMR (DMSO-d$_6$): δ=8.1–7.7 m (15H); 6.3 m (1 H); 2.55 dd (3H)).

Scheme 2

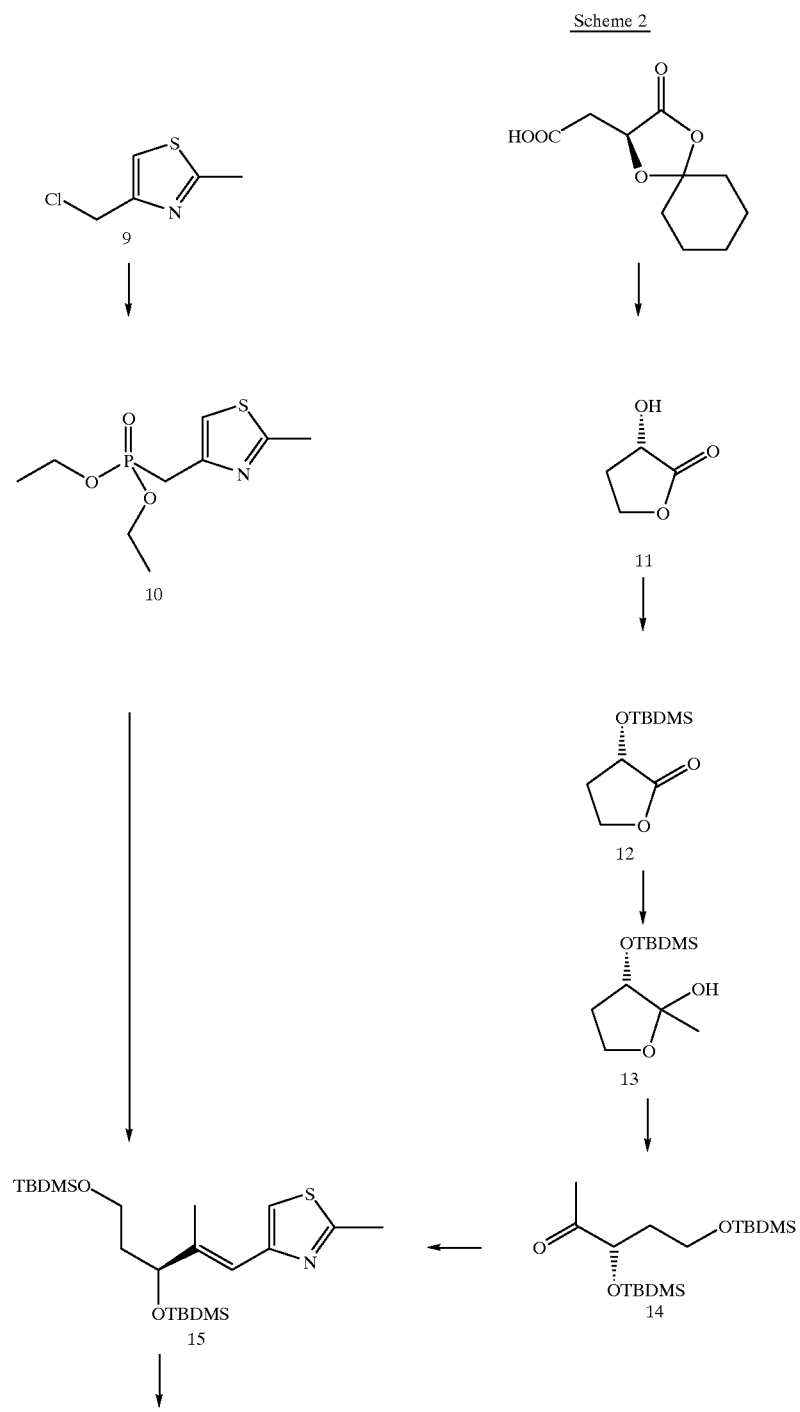

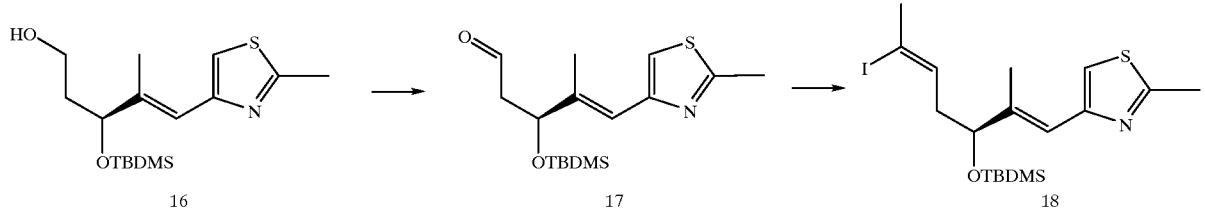

Preparation of 18 can then be carried out as follows:

0.600 ml of a 1M solution of NaHMDS in THF are added at −78° to a suspension of 0.680 g of iodoethyl phosphonium iodide in 20 ml of THF. After stirring at −78° for 30 min, the yellow suspension is allowed to warm to −15° over a period of 10 min, resulting in the formation of a red solution. After 20 min at −15° the solution is again cooled to −78° and 0.325 g of aldehyde 17 are added at this temperature. After 20 min at −78°, the reaction is quenched by adding 5 ml of saturated aqueous $NH_4Cl$ at −78° and then worked up as described above.

3) Pd Coupling and Transformation of the Coupling Product (Scheme 5)

a) (6S,10S,2Z,6E)-3,11-Di(tert-butyldimethylsilyioxy)-1-(2-methylthiazol-4-yl)-2,6,10-trimethyl-undeca-1,5-diene 19

1,2-Dibromoethane (35 µl) is added to a suspension of powdered Zn/Cu couple [J. E. McMurry, J. G. Rico: Tetrahedron Lett. 30, 1169–1172 (1989)] (477 mg, 7.27 mmol, 2.3 equiv) in 11 ml of benzene under argon. The mixture is heated for a few seconds under reflux. After cooling to r.t., chlorotrimethylsilane (35 µl) is added and the mixture is stiffed for 5 min. N,N-dimethylacetamide (750 µl) and (S)-1-Iodo-5-(tert-butyl-dimethylsilyloxy)-4-methyl-pentane 8 (1.623 g, 4.74 mmol, 1.5 equiv) in 4.0 ml of benzene is added. The mixture is stirred for 2 h 30 min at 60° C. and analyzed by tic If starting material can still be detected, triethylsilyl trifluoromethanesulfonate (20 µl) or a few mg of mercury(II) acetate (for further activation of the metal) and 750 µl of N,N-dimethylacetamide is added, and the mixture is heated under reflux for 1 h. After cooling to r.t., $Pd(PPh_3)_4$ (140 mg, 4mol-%) is added and the mixture is stirred for 5 min. A solution of (S,2Z,6E)-5-(tert-butyldimethylsilyloxy)-2-iodo-6-methyl-7-(2-methylthiazol-4-yl)-hepta-2,6-diene 18 (1.463 g, 3.16 mmol) in 3.0 ml of benzene is added and the mixture is stirred for 30 min at 60° C. After cooling to r.t., the reaction is quenched with saturated aqueous ammonium chloride solution (5 ml). The organic layer is separated and the aqueous layer is extracted with methyl tert-butyl ether (3×30 ml). The combined organic layers are dried over magnesium sulfate and concentrated in vacuo. Purification of the residue by flash column chromatography (pentane/diethyl ether 25:1) affords (6S,10S,2Z,6E)-3,11-di-(tert-butyidimethylsilyloxy)-1-(2-methylthiazol-4-yl)-2,6,10-trimethyl-undeca-1,5-diene 19 (1.458 g, 84%) as a colourless oil. Alternatively, benzene can be replaced by THF in the reaction. The yields decrease to 64%.=>for spectroscopical data cf. ref. [K. C. Nicolaou et al., J. Am. Chem. Soc. 119, 7974–7991 (1997)].

b) (6S,10S,2Z,6E)-3(tert-Butyldimethylsilyloxy)-1-(2-methylthiazol-4-yl)-2,6,10-trimethundeca-1,5-dien-11-ol 20

The synthesis is carried out according to the Nicolaou procedure, see K. C. Nicolaou et al., J. Am. Chem. Soc. 119, 7974–7991 (1997) by reaction in methylene chloride:methanol (1:1, v/v) in the presence of campher sulfonic acid.

Scheme 5

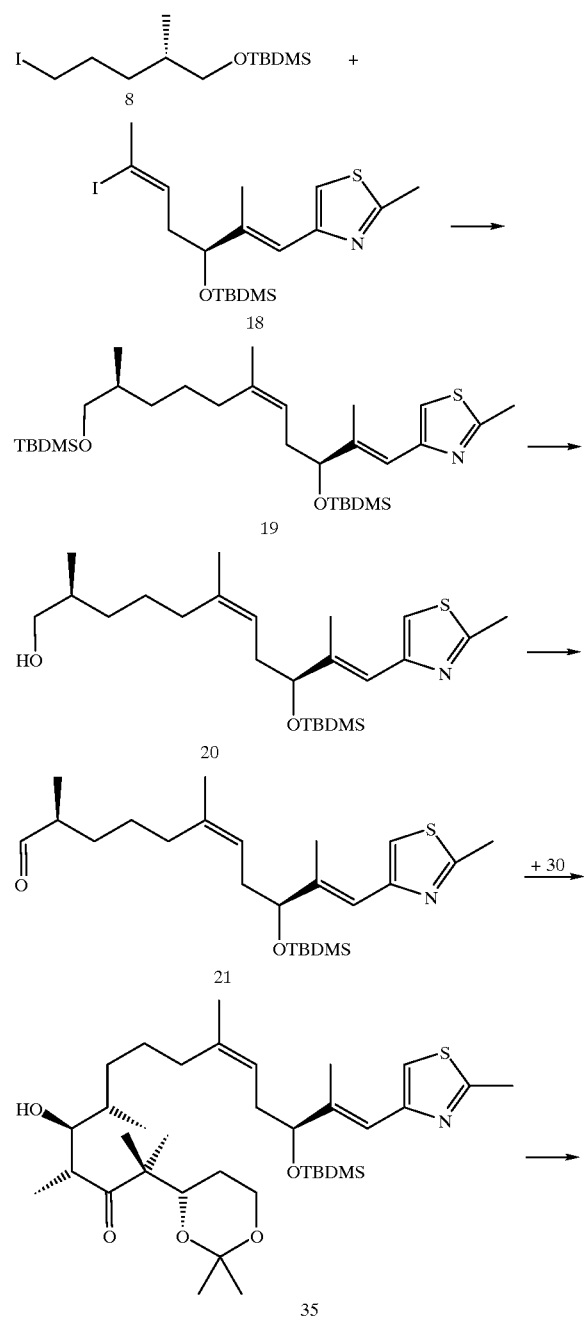

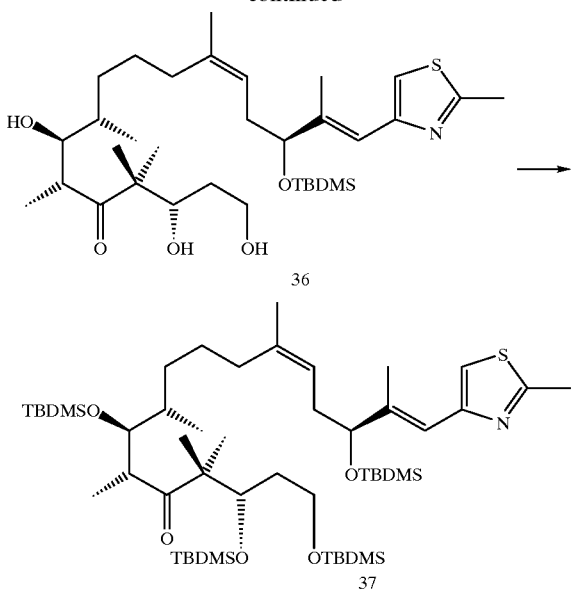

c) (6S,10S,2Z,6E)-3-(tert-Butyldimetylsilyloxy)-1-(2-methylthiazol-4-yl)-2,6,10-trimethylundeca-1,5-dien-11-al 21

A solution of (6S,10S,2Z,6E)-3(tert-butyldimethylsilyloxy)-1-(2-methylthiazol-4-yl)-2,6,10-trimethyl-undeca- 1,5-dien-11-ol 20 (306 mg, 0.7 mmol) in 5.0 ml of dichloromethane is added dropwise to a stirred solution of the Dess-Martin periodinane (386 mg, 0.91 mmol, 1.3 equiv) in 5.0 ml of dichloromethane and 73 μl (0.91 mmol) of pyridine cooled to 0° C. The mixture is stirred for 30 min at r.t. Diethyl ether (30 ml), pyridine (146 μl, 1.82 mmol) and 0.5 M buffered (pH 7) aqueous sodium thiosulfate solution (10 ml) are added. The organic layer is separated off, and the aqueous layer is extracted with methyl terbutyl ether (2×20 ml). The combined organic layers are dried over magnesium sulfate and concentrated in vacuo. Purification of the residue by flash column chromatography (pentane/diethyl ether 5:1) affords (6S,10S,2Z,6E)-3(tert-butyldimethylsilyloxy)-1-(2-methylthiazol-4-yl)-2,6,10-trimethylundeca-1,5-dien-11-al 21 (295 mg, 97%) as a pale yellow oil; $^{13}$C-NMR: δ=205.2; 164.4; 153.0; 142.0; 130.6; 126.4; 118.8; 115.0; 78.7; 46.2; 34.7; 30.0; 27.3; 26.9; 25.8; 19.2; 18.2; 13.9; 13.2; −4.7; −5.0.

4) The HYTRA Route to the Ethyl Ketone (Scheme 4)

(see P. Eilbracht et al., Chem. Ber. 122, 151–158 (1989))

a) Ethyl 2,2-dimethyl-3-ethyl-3-hydroxypentanoate 22

A suspension of zinc dust (39.2 g, 0.6 mol) in 150 ml of THF and 150 ml of B(OCH$_3$)$_3$ is activated with 1,2 dibromoethane (3.0 ml) and chlorotrimethylsilane (3.0 ml). Diethyl ketone (95.7 ml, 0.9 mol) is added to the activated zinc suspension. Ethyl 2-bromo-2-methylpropanoate (Fuka, Buchs, Schweiz) is added dropwise within 90 min to the mixture. The mixture is stirred at r.t. for 20 h. The reaction is quenched by addition of concentrated aqueous ammonia solution (150 ml) at 0° C. Glycerine (150 ml) and diethyl ether (150 ml) is added and the organic layer is separated. The aqueous layer is extracted twice with diethyl ether. The combined organic layers are dried over magnesium sulfate and concentrated in vacuo. Purfication of the residue by vacuum distillation affords ethyl 2,2-dimethyl-3-ethyl-3-hydroxypentanoate 22 (56.65 g, 47%) as a colourless liquid (b.p. 108–110° C./10 mbar). $^{13}$C-NMR (100 MHz, CDCl$_3$): δ=179.2; 76.2; 60.9; 50.3; 28.2; 21.6; 14.1; 8.9 b) Ethyl (E)-2,2-Dimethyl-2-ethyl-3-pentenoate 23

Ethyl 2,2-dimethyl-3-ethyl-3-hydroxypentanoate 22 (56.64 g, 280 mmol) is heated under reflux with phosphorous pentoxide (50.4 g, 355 mmol) in benzene (200 ml) for 15 min. Benzene is distilled off. The residue is extracted with diethyl ether (3×100 ml) and dissolved in saturated aqueous sodium bicarbonate solution (150 ml) at 0° C. The resulting solution is neutralized by carefully adding sodium carbonate and extracted with diethyl ether (3×100 ml). The combined etheral extracts are dried over magnesium sulfate and concentrated in vacuo. Purification of the residue by vacuum distillation affords the title compound 23 (36.09 g, 70%) as a colourless liquid (b.p. 60–63° C./3 mbar). $^{13}$C-NMR (100 MHz, CDCl$_3$): δ=177.2; 144.1; 118.5; 60.3; 48.4; 24.9; 21.7; 14.1; 13.9; 13.5 c) (E)-2,2-Dimethyl-3-ethyl-3-penten-1-ol 24

Ethyl (E)-2,2-dimethyl-3-ethyl-3-pentenoate 23 (35.58 g, 193 mmol) is added dropwise to a suspension of lithium aluminium hydride (12.1 g, 320 mmol) in 81 ml of THF. The mixture is refluxed for 3 h, stirred for 16 h at r.t. and quenched with ice. The precipitate is filtered off by suction, washed several times with diethyl ether and hydrolyzed with 1 M hydrochloric acid. The aqueous solution is extracted with diethyl ether (3×100 ml). The combined etheral extracts are dried over magnesium sulfate and concentrated in vacuo. Purification of the residue by vacuum distillation affords the title compound 24 (15.87 g, 58%) as a colourless liquid (b.p. 105–106° C./30 mbar). $^{13}$C-NMR (100 MHz, CDCl$_3$): δ=145.2; 120.5; 69.7; 42.0; 24.0; 20.0; 14.2; 13.6 d) (E)-2,2-Dimethyl-3ethyl-3-pentenal 25

A solution of dimethyl sulfoxide (18.7 ml, 260 mmol) in 80 ml of dichloromethane is added dropwise within 5 min to a stirred solution of oxalyl chloride (11 ml, 130 mmol) in 400 ml of dichloromethane cooled to −78° C. The mixture is stirred for 10 min at −70° C. A solution of (E)-2,2-Dimethyl-3-ethyl-3-penten-1-ol 24 (15.57 g, 110 mmol) in 60 ml of dichloromethane is added dropwise within 5 min. The mixture is stirred for 1 h at −70° C. The reaction is quenched by dropwise addition of triethyl amine (76.3 ml, 550 mmol). The mixture is warmed to r.t. within 45 min. Water (400 ml) is added and the mixture is stirred for 10 min. The organic layer is separated off, and the aqueous layer is extracted with diethyl ether (3×200 ml). The combined organic extracts are dried over magnesium sulfate and concentrated in vacuo. Purification of the residue by vacuum distillation affords the title compound 25 (9.7 g, 63%) as a colourless liquid (b.p. 85–86° C./28 mbar). $^{13}$C-NMR (100 MHz, CDCl$_3$): δ=203.5; 141.4; 122.6; 52.7; 24.2; 20.9; 14.1; 13.8 e) (1S)-(1,2,2-Triphenyl-2-hydroxyethyl-)(3S,E)-4,4dimethyl-5ethyl-3-hydroxy-5-heptenoate 26

3.20 ml (8.0 mmol) of a 2.5 M solution of n-butyl lithium in hexanes at −78° C. is added to a solution of diisopropylamine (1.28 ml, 8.0 mmol) in 10 ml of THF cooled to −78 ° C. The LDA solution is stirred for 30 min at 0° C. and added dropwise to a solution of (S)-(−)-2-hydroxy-1,2,2-triphenyl acetate (1.330 g, 4.0 mmol) in 25 ml of THF at −78° C. The mixture is stirred for 1 h at 0° C. The resulting orange-red solution is cooled to −78° C., and a solution of (E)-2,2-Dimethyl-3-ethyl-3-pentenal 25 (673 mg, 4.8 mmol, 1.2 equiv) in 5.0 ml of THF is added dropwise. The mixture is stirred for 90 min. The reaction is quenched with saturated aqueous ammonium chloride solution (30 ml). The organic layer is seperated and the aqueous layer is extracted with dichloromethane (3×50 ml). The combined organic extracts are dried over magnesium sulfate and concentrated in vacuo. Purification of the residue by flash column chromatography (pentane/diethyl ether 3:1) affords the title compound 26 (1.41 g, 75%, 94% de) as a colourless crystalline solid (m.p.100° C.). $^{13}$C-NMR (100 MHz, CDCl$_3$): δ=172.2; 146.0; 144.7; 142.6; 135.6; 128.4; 128.3; 128.0; 127.8; 127.5; 127.3; 127.1; 126.3; 126.2; 120.3; 80.4; 78.9; 72.3; 44.0; 37.4; 21.9; 21.3; 20.2; 14.3; 13.6

[f) (E)-4,4-Dimethyl-5-ethyl-3S-hydroxyhept-5-enoic Acid 27

Potassium hydroxide (163 mg, 2.5 mmol) is added to a solution of the ester (1.182 g, 2.5 mmol) in 29 ml of methanol and 8.3 ml of water. The mixture is heated under reflux for 2 h, cooled to r.t. and concentrated in vacuo. The resulting suspension is filtered by suction. The solid is washed with 50 ml of water. The combined aqueous layers are extracted with dichloromethane (2×50 ml) to remove traces of (S)-2,2,1-triphenyl ethanediol. The aqueous solution is cooled to 0° C. and acidified to pH 2.5 by dropwise addition of 6 N hydrochloric acid with vigorous stirring. The clear solution is saturated with solid sodium chloride and extracted with ethyl acetate (5×50 ml). The combined organic extracts are dried over magnesium sulfate and concentrated in vacuo. After complete evaporation, (E)-4,4-dimethyl-5-ethyl-3S-hydroxyhept-5-enoic acid 27 (442 mg, 88%) is obtained as a colourless crystalline solid. $^{13}$C-NMR (100 MHz, CDCl$_3$): δ=178.5; 145.8; 121.0; 72.2; 44.0; 36.7; 22.5; 21.8; 20.4; 14.3; 13.7]

g) (S)-(E)-4,4-Dimethyl-5-ethyl-5-heptene-1,3-diol 28

Lithium aluminium hydnde (1.325 g, 35.0 mmol, 7.0 equiv) is added portionwise to a refluxing solution of (1S)-2,2,1-triphenyl-2-hydroxyethyl (3S,E)-4,4-dimethyl-5-ethyl-3-hydroxy-5-heptenoate 26 (2.364 g, 5.0 mmol) in diethyl ether (50 ml) within a period of 2 h. Refluxing is continued for 30 min. After cooling to 0° C., the reaction is quenched dropwise with 1.35 ml water and 1.35 ml of aqueous NaOH (15%). Diethyl ether (40 ml) and water (2.0 ml) is added. The mixture is stirred for 1 h at r.t. until a white precipitate forms which is filtered off by suction through a small plug of celite. The precipitate is washed with diethyl ether (4×40 ml). The filtrate and the washings are combined and concentrated in vacua. Purification of the residue by flash column chromatography (pentane/diethyl ether 2:1) affords (S)-2,2,1-Triphenyl-ethane-1,2-diol (922 mg, 99%) as a colourless, crystalline solid and (S)-(E)-4,4-Dimethyl-5-ethyl-5-heptene-1,3-diol 28 (836 mg, 90%) as a colourless oil. $^{13}$C-NMR (100 MHz, CDCl$_3$): δ=146.2; 121.1; 75.8; 62.6; 44.4; 32.7; 22.8; 21.1; 20.1; 14.3; 13.6 h) (S)-(E)-4-(2,2-Dimethyl-[1,3]dioxan-4-yl)-3-ethyl-2-methyl-pent-3-ene 29

Anhydrous copper sulfate (478 mg, 3.0 mmol, 1.5 equiv), p-toluenesulfonic acid monohydrate (76 mg, 0.4 mmol, 0.2 equiv), and pyridine (24 μl, 0.3 mmol, 0.15 equiv) are added to a solution of (S)-(E)-4,4-dimethyl-5-ethyl-heptane-1,3-diol 28 (372 mg, 2.0 mmol) in acetone (30 ml). The mixture is stirred for 24 h at r.t. Saturated aqueous sodium bicarbonate solution (40 ml) is added, and the aqueous layer is extracted with diethyl ether (4×60 ml). The combined organic extracts are dred over magnesium sulfate and carefully concentrated in vacuo. Purification of the residue by flash column chromatography (pentane/diethyl ether 40:1) affords the title compound 29 (812 mg, 90%) as a colourless oil. $^{13}$C-NMR (50 MHz, CDCl$_3$): δ=146.2; 119.3; 98.3; 74.2; 60.4; 42.9; 29.9; 26.2; 24.3; 21.2; 19.2; 14.4; 13.7 i) (S)-2(2,2-Dimethyl-[1,3]dioxan-4-yl)-2-methyl-pentan-3-one 30 ("ethyl ketone")

Ozone in oxygen is bubbled through a stirred solution of (S)-(E)-4-(2,2-dimethyl-[1,3]dioxan-4-yl)-3-ethyl-4-methyl-pent-2-ene 29 (226 mg, 1.0 mmol) in dichloromethane (40 ml) at −78° C. until the blue colour of ozone persists. Triphenyl phosphine (262 mg, 1.2 equiv) is added. The reaction mixture is warmed to r.t. within 4 h and concentrated in vacua. Purification of the residue by flash column chromatography (pentane/diethyl ether 5:1) affords (S)-2(2,2-dimethyl-[1,3]dioxan-4-yl)-2-methyl-pentan-3-one 30 (182 mg, 85%) as colourless crystals. $^{13}$C-NMR (CDCl$_3$) δ=213.2; 98.4; 74.2; 59.8; 50.; 31.7; 30.0; 25.6; 21.0; 19.4; 19.0; 8.2.

Scheme 4

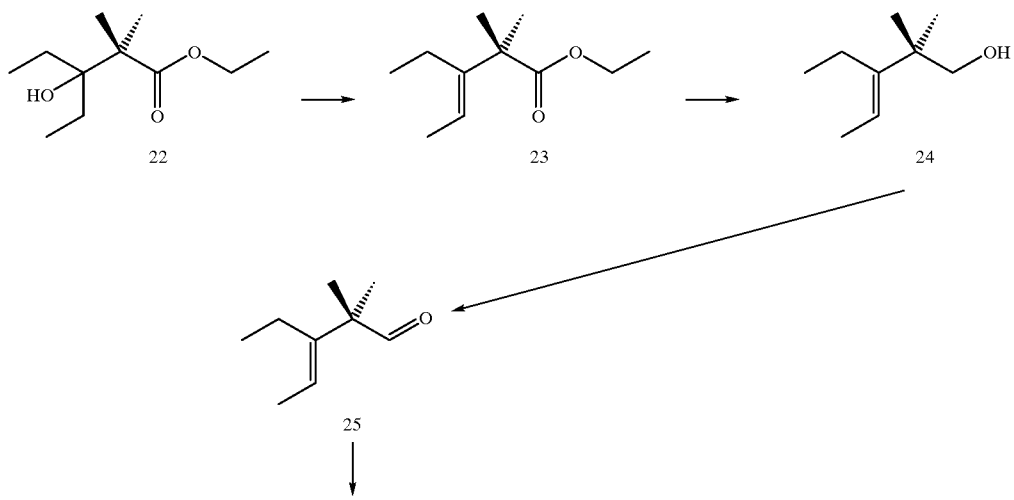

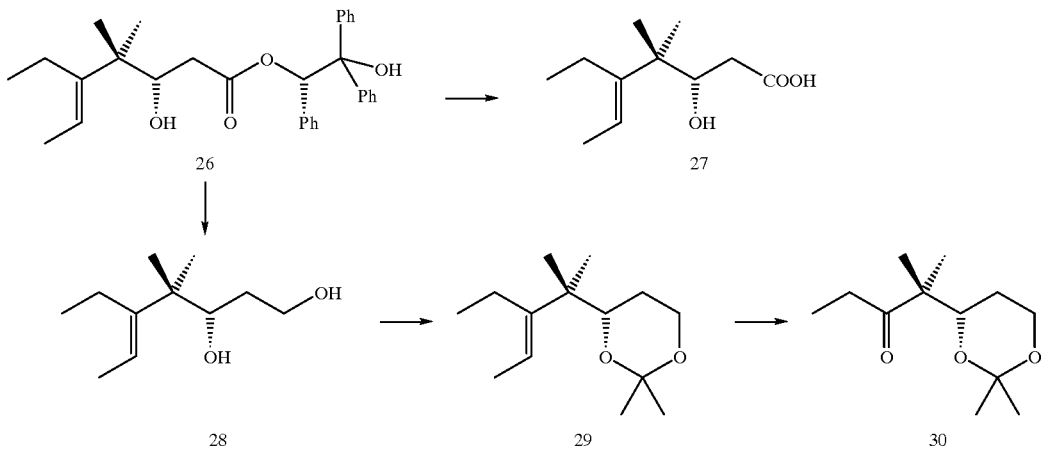

5. Alternative Synthesis of Compound 30 (Scheme 3):

a) Compound 31:

Under an Ar atmosphere, 336 ml of triethyl borane are added slowly to 2.5 l of hexane at room temperature (ca. 25 min). To this solution, 187 ml of $CF_3SO_3H$ are added under cooling. After rinsing the dropping funnel with 180 ml of dichloromethane, the mixture is slowly warmed to 40° until gas evolution ceases (ca. 70 min). It is then cooled and a solution of 459 g of (2R)-N-acetylbomane-10,2-sultam (W. Oppolzer et al., *Tetrahedron Lett.* 1992, 33, 2439) in 4 l of dichloromethane is added at 0°–2° over a period of 20 min followed by a solution of 382 ml of diisopropylethyl amine (Hünig's base) in 1.5 l of dichloromethane (also at 0°–2°; ca 20 min). The reaction mixture is then cooled to –75° and a solution of 329 g of 2,2-dimethyl-3-oxo-pentanal (K. C. Nicolaou et al., *J. Am. Chem. Soc.* 1997, 119,7974) in 300 ml of dichlormethane is added at the same temperature over a period of 35 min. After an additional 1.5 h at –70°–75°, the reaction is quenched by addition of 400 ml of THF/water 3/1 followed by 3.5 l of saturated aqueous $NH_4Cl$. The solution is then concetrated and diluted with 2 l of ethyl acetate plus 2 l of water, and the organic layer is separated off. The remaining a aqueous solution is extracted three times with 2 l of ethyl acetate, respectively, and the combined organic extracts are washed with 6 times with 1 l of water and then once with 1 l of brine. Drying over $Na_2SO_4$ and evaporation of solvent gives a semi-crystalline yellow residue which is then recrystallized twice from ethylacetateihexane to yield 3.16 g of 31 as a single diastereoisomer (white crystals). M.p.: 121–122° C. MS ($C_{19}H_{31}NO_5S$; 385.52): 386 [M+H]. $^1$H-NMR ($CDCl_3$): δ=4.3 m (1H); 3.85 m (1H); 3.45 dd (2H); 3.25 m (1H); 2.9–2.65 m (2H); 2.55 q (2H).

b) Compound 32:

To a solution of 409 g of compound 31 in 3 l of dichlormethane, 185 ml of 2,6-lutidine are added, followed by a solution of 292 ml of t-butyl-dimethylsilyl triflate in 200 ml of dichloromethane (both additons at approximately –75°). The reaction mixture is stirred at –75° for 2.5 h and then allowed to warm to room temperature over night. Then, the mixture is extracted three times with 1 l of water, respectively, the combined aqueous extracts are re-extracted twice with each time 1 l of dichloromethane, and the combined organic extracts are finally evaporated to dryness. The residue is recrystallized from ethanol/water to yield 485 g of 32 as white crystals. M.p.: 87–89° C. MS ($C_{19}H_{45}NO_5SSi$; 499.78): 500 [M+H]. $^1$H-NMR ($CDCl_3$):

δ=4.75 m (1H); 3.8 m (1H); 3.4 dd (2H); 2.95dd (1H); 2.75 dd (1H); 2.5 q (2H); 0.8 s (9H).

c) 3(S)-(tert-Butyl-dimethyl-silyloxy)-4,4-dimethyl-5-oxo-heotanoic Acid 33:

To a solution of 10 g of compound 32 in 100 ml of THF/water 4/1, 0.772 g of LiOH are added, followed by 3.37 ml of 30% aqu. $H_2O_2$. After 7 h stirring at room temperature, 3.78 g of $Na_2SO_3$ are added to the mixture and the THF is removed by evaporation. 50 ml of ethyl acetate are added to the remaining aqueous suspension and the pH is adjusted to 6 by addition of 1 N HCl. The organic layer is then removed and the aqueous solution is extracted twice with ethyl acetate. The combined organic extracts are evaporated and the residue is suspended in 50 ml of hexane. After stirring at 0° C. for 1 h the mixture is filtered, the filtrate evaporated and the residue purified by Flash Chromatography in dichloromethane/MeOH 9713→95/1 to yield 4.58 g of 33 as an oil. $^1$H-NMR ($CDCl_3$): δ=4.45 m (1H); 3.6–3.4 m (3H); 2.3 dd (1H); 1.15 s (3H); 1.05 s (3H); 1.00 t (3H); 0.85 s (9H).

d) 5(S)-(tert-Butyl-dimethyl-silyloxy)-7-hydroxy-4,4-dimethyl-heptan-3-one 34:

1.017 ml of trimethyl borate, followed by 0.607 ml of $BH_3 \times Me_2S$. are added to a solution of 0.689 g of compound 33 in 20 ml of THF at 0°. The reaction mixture is stirred at 0° for 2 h and at 15° for 6 h. It is then cooled to 0°, 3 ml of water are added dropwise and the mixture is stirred for 10 min. The solvents are subsequently evaporated and the residue is re-evaporated three times after addition of methanol and then purified by flash chromatography using dichloromethanel ether 98/2 to give 0.71 g of 34 as an oil. MS ($C_{15}H_{32}O_3Si$; 288): 271 [M–OH]; 231 [M-t-butyl].

Scheme 3

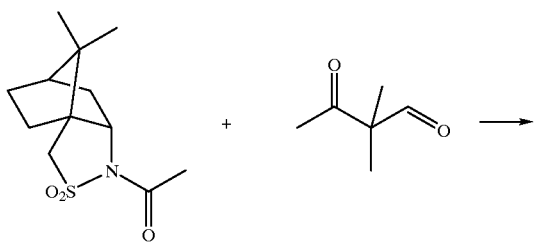

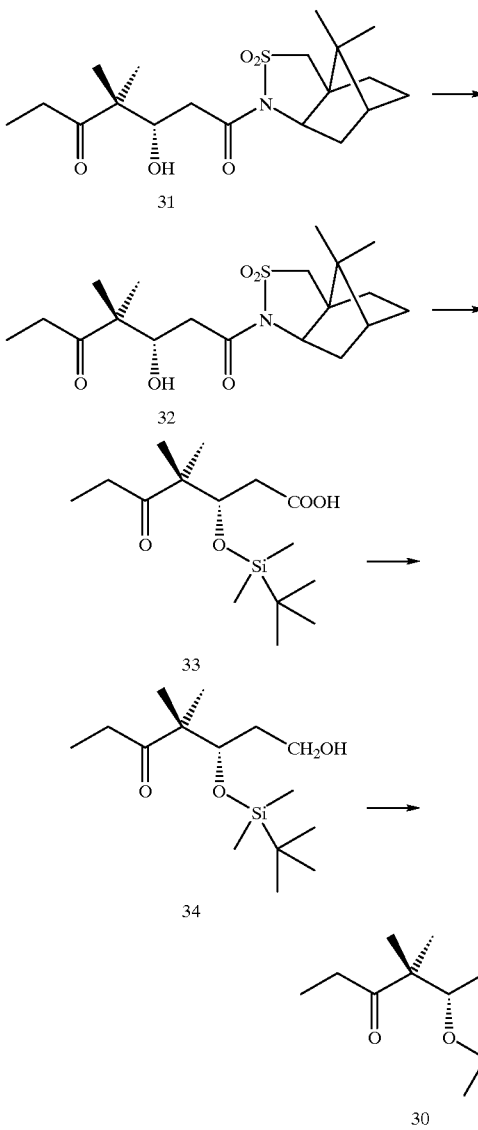

e) (S)-2(2,2-Dimethyl-[1,3]dioxan-4-yl)-2-methyl-pentan-3-one 30:

A solution of 0.200 g of compound 34 in 5 ml of acetone/CF₃COOH is heated to 35° for 18 h. Trethyl amine (1 ml) is then added to the mixture at 0° followed by 20 ml of diethyl ether. The solution is then three times extracted with 10 ml of water each, dred, and the solvent evaporated. FC of the residue in hexanelether 3/1 (+1% of triethyl amine) gives 0.118 g of 30. MS (C₁₂H₂₂O₃; 214): 215 [M+H]. ¹H-NMR (CDCl₃): δ=4.05–3.80 m (3H); 2.5 q (2H); 1.40 s (3H); 1.30 m (includ. s) (4H); 1.10 s (3H); 1.00 s (3H); 0.95 t (3H).

6) The Aldol Reaction and the Final Steps to of the Formal Total Synthesis of Epothilone B (Scheme 5)

a) The Aldol Reaction to yield compound 35

A solution of (S)-2(2,2-Dimethyl-[1,3]dioxan-4-yl)-2-methyl-pentan-3-one 30 (64 mg, 0.3 mmol) in THF (500 μl) is added dropwise at −78° C. to a freshly prepared solution of LDA [n-BuLi (118 μl, 2.5 m solution in hexanes, 0.294 mmol, 0.98 equiv) is added to a solution of diisopropylamine (41.6 μl, 0.294 mmol) in THF (500 μl) at 0° C. The mixture is stirred for 30 min at 0° C.]. Then, the solution is stirred for 1 h at −78° C. A solution of (6S,10S,2Z,6E)-3-(tert-butyldimethyl-silyloxy)-1-(2-methylthiazol-4-yl)-2,6,10-trimethyl-undeca-1,5-dien-11-al 21 (65 mg, 0.15 mmol, 0.5 equiv) in THF (600 μl) is added dropwise, and stirring is continued for 20 min at −78° C. The mixture is quenched by dropwise addition of saturated aqueous ammonium chloride solution (2 ml). The organic layer is seperated and the aqueous layer is extracted with diethyl ether (3×5 ml). The combined organic extracts are dried over magnesium sulfate and concentrated in vacuo. Purification of the residue by flash column chromatography (pentane/diethyl ether 10:1, then 5:1) affords 83 mg (85%) of 35 as colourless oil. Maior diasteroisomer: ¹³C-NMR (100 MHz, CDCl₃): δ=222.81; 164.27; 153.28; 142.49; 136.94; 121.44; 118.65; 114.89; 98.45; 79.08; 74.74; 74.38; 59.89; 51.60; 41.28; 35.42; 35.32; 33.04; 32.40; 29.76; 25.85; 25.24; 25.15; 23.51; 21.55; 19.19; 19.03; 18.58; 18.24; 15.35; 13.92; 9.31; −4.65; −4.93 b) Triol Compound 36

PPTS (6.0 mg, 24 μmol, 0.6 equiv) is added to a solution of the ANTICRAM aldol product 35 (26 mg, 0.04 mmol) in methanol (500 μl). The mixture is stirred for 22 h. Another portion of PPTS (4.0 mg, 16 μmol, 0.4 equiv) is added and stirring is continued for 50 h. The solvent is removed in vacuo and the residue is purified by flash column chromatography with diethyl ether. The triol 36 (21 mg, 86%) is obtained as a colourless oil. ¹³C-NMR (CDCl₃) δ=223.3; 154.5; 153.1; 142.7; 136.8; 121.6; 118.7; 114.8; 79.2; 76.3; 74.4; 62.1; 52.7; 41.1; 35.6; 35.4; 32.8; 32.5; 32.3; 25.8; 25.1; 23.5; 21.6; 19.1; 18.5; 18.2; 15.5; 13.8; 10.1; −4.0; −4.3.

c) Tetrakis Silyl Ether 37 (Compound of Formula I Wherein Each of X₁ to X₄ is tert-Butyldimethylsilyl and R is 2-Methylthiazol-4-yl)

2,6-lutidine (29 μl, 247.5 μmol, 2.5 equiv) is aded to a solution of the triol 32 (20.0 mg, 33 μmol) in dichloromethane (200 μl). The mixture is cooled to −50° C. and tert-butyl-dimethylsilyltrifluormethanesulfonate (34 μl, 148.5 μmol, 1.5 equiv) is added. The mixture is warmed 0° C. and stirring is continued for 2 h at 0° C. The solvent is removed in vacuo and the residue is purified by flash column chromatography (pentane/diethyl ether 20:1). The tetrakis silyl ether 33 (30 mg, 95%) is obtained as a colourless oil. ¹³C-NMR (100 MHz, CDCl₃): δ=218.25; 164.27; 153.29; 142.49; 136.75; 121.56; 118.68; 114.90; 78.99; 77.45; 74.04; 60.99; 53.66; 45.05; 38.95; 38.11; 35.34; 32.57; 31.04; 29.70; 26.24; 26.12; 25.97; 25.85; 24.50; 23.53; 19.40; 19.22; 18.52; 18.30; 18.24; 18.13; 17.56; 15.20; 13.93; −3.65; −3.67; −3.75; −3.98; −4.64; −4.92; −5.22; −5.25

What is claimed is:

1. A method of synthesis of a compound of the formula XX,

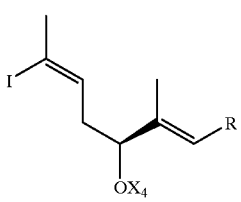

(XX)

wherein R is a heterocyclic moiety and X₄ is a protecting group, characterized in that a compound of the formula XIX

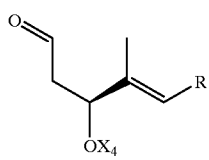
(XIX)

wherein R and $X_4$ are as defined under formula XX, is, by reaction with an strong base and iodine in the presence of triphenylphosphonium iodide and subsequent addition of the same or another strong base as above converted into a compound of the formula XX.

2. A method of synthesis of a compound of the formula XIV,

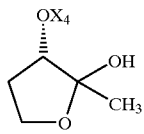
(XIV)

wherein $X_4$ is a protecting group, characterized in that a compound of the formula XIII,

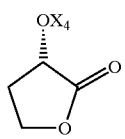
(XIII)

wherein $X_4$ is a protecting group, is reacted with an methyl metal or methyl metal derivative.

3. A compound of the formula

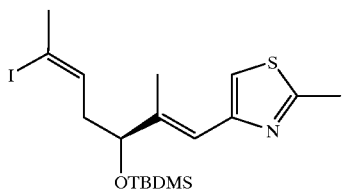
18 wherein TBDMS is tert-butyldimethylsilyl.

4. A compound of the formula XIV

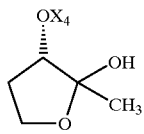
(XIV)

wherein $X_4$ is a protecting group other than tert-butyldimethylsilyl.

5. A method of synthesis for a compound of the formula XXIV,

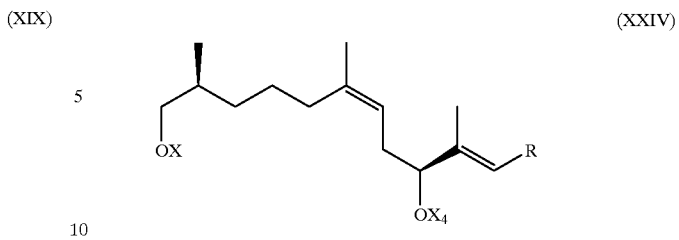
(XXIV)

wherein X and $X_4$ each are a protecting group, and R is a heterocyclyl moiety, characterized in that a compound of the formula X

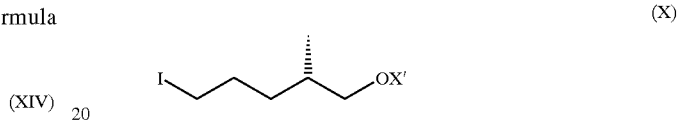
(X)

wherein X' is a protecting group, is coupled by reaction with a suspension of powdered Zn/Cu couple in the presence of an activator and of a halotrialkylsilane, and then addition of a Pd(0)-complex in an appropriate solvent, with a compound of the formula XX

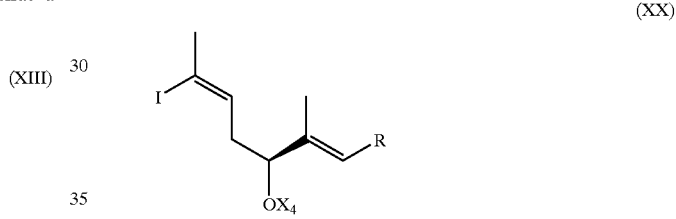
(XX)

wherein $X_4$ is a protecting group and R is a heterocyclyl moiety.

6. A compound of the formula

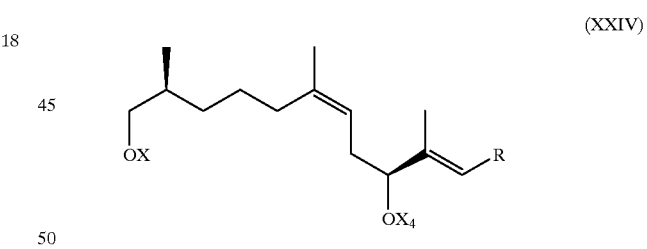
(XXIV)

wherein X and $X_4$ each are a protecting group, and R is a heterocyclyl moiety, in the essentially pure cis-form.

7. A compound of the formula XXV,

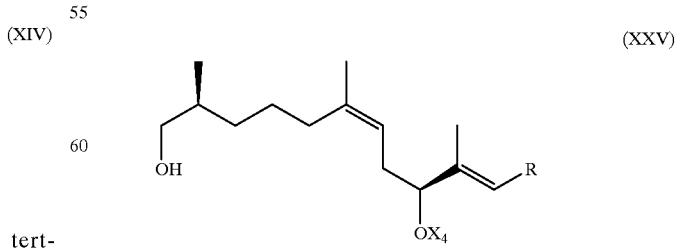
(XXV)

wherein $X_4$ is a protecting group and R is a heterocyclyl moiety in the essentially pure cis-form.

8. A compound of the formula XXVII, (XXVII)

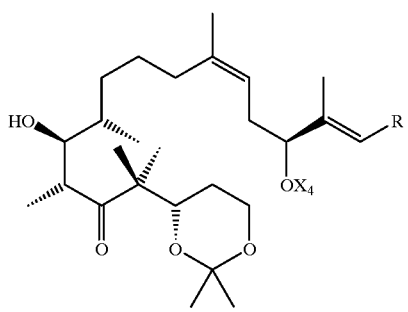

wherein $X_4$ is a protecting group and R is a heterocyclyl moiety.

9. A new process for preparing a compound of formula I (I)

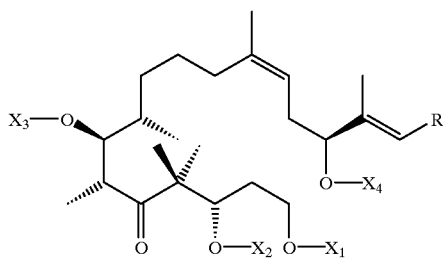

wherein R is a heterocyclyl moiety and $X_1$, $X_2$, $X_3$ and $X_4$ are, independently of each other, protecting groups, which comprises: 1) in a first step, adding tetrakis-triphenylphosphine palladium (O)-catalyst in an appropriate solvent and a compound of formula XX (XX)

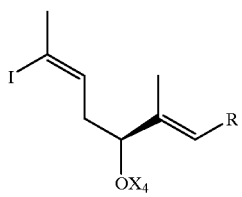

wherein R and $X_4$ are as defined above, to the product obtained by reacting an iodide compound of formula X (X)

wherein X' is a protecting group as defined for $X_1$ to $X_4$, with a suspension of powdered Zu/Cu couple in the presence of an activator and a halotrialkylsilane to obtain a compound of formula XXIV (XXIV)

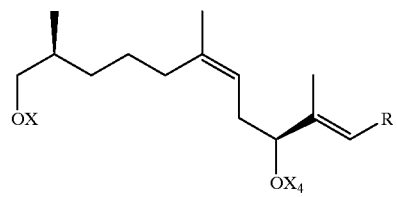

wherein R and $X_4$ are as defined above and X is a protecting group as defined above $X_1$ to $X_4$; 2) in a second step, selectively de-protecting a compound obtained in the first step to obtain a compound of formula XXV (XXV)

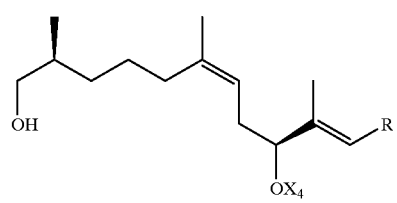

wherein R and $X_4$ are as defined above; 3) in a third step, oxidizing a compound obtained in the second step with an appropriate oxidant to obtain the corresponding aldehyde of formula XXVI (XXVI)

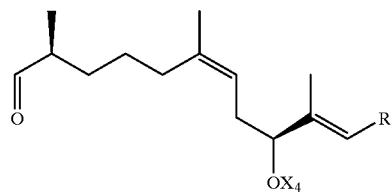

wherein R and $X_4$ are as defined above; 4) in a fourth step, reacting a compound obtained in the third step with (S)-2-(2,2-dimethyl-[1,3]dioxan-4-yl)-2-methyl-pentan-3-one in an Aldol reaction to obtain a compound of formula XXVII (XXVII)

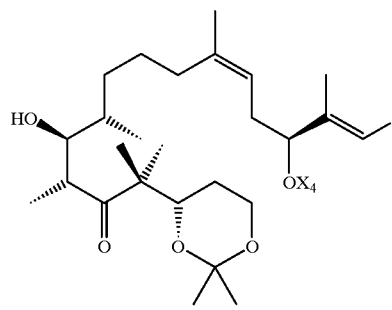

wherein R and $X_4$ are as defined above; 5) in a fifth step, de-protecting a compound obtained in the fourth step by removal of the acetal moiety to obtain a compound of formula XXVIII (XXVIII)

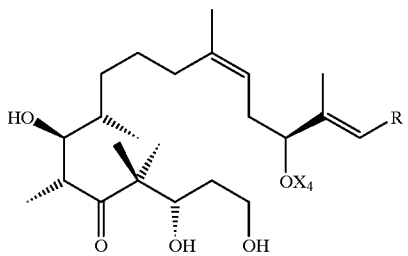

wherein R and $X_4$ are as defined above; and 6) in a sixth step, introducing protecting groups $X_1$, $X_2$ and $X_3$ in a compound obtained in the fifth step with appropriate reagents to obtain a compound of formula I;

said iodide compound of formula X is obtained by a process which comprises: 1) in a first step, reacting a compound of formula II (II)

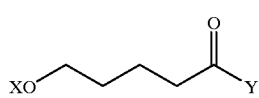

wherein y is the radical of an organic or inorganic acid devoid of its dissocialable hydrogen, and X is a protecting group as described above for $X_1$ to $X_4$, with an oxazolidone of the formula III (III)

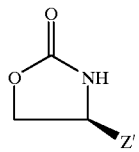

wherein Z' is lower alkyl or phenyl-lower alkyl in an appropriate solvent and in the presence of either (i) a strong base initially and then a teriary amino base; or (ii) an alkali metal alkylid, at low temperatures to obtain a compound of formula IV (IV)

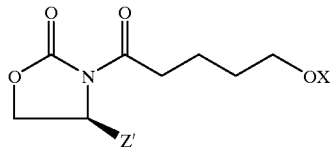

wherein X and Z' are as defined above; 2) in a second step, C-methylating a compound obtained in the first step in the presence of a strong base to obtain a compound of formula V (V)

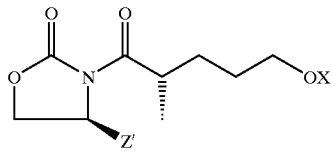

wherein X and Z' are defined as above; 3) in a third step, subjecting a compound obtained in the second step to reductive cleavage to release a compound of formula VI (VI)

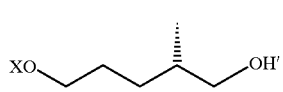

where X is as defined above; 4) in a fourth step, introducing a protecting group X' selected from the protecting groups as described above for $X_1$ to $X_4$, but different from X in formula VI, at the free hydroxyl group of the compound obtained in the third step which allows the protecting group X in the compound of formula VI to be cleaved off without affecting the newly introduced protecting group to obtain a bis-protected compound of formula VII (VII)

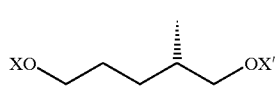

wherein X and X' are as defined above; 5) in a fifth step, cleaving the protecting group X in the compound obtained in the fourth step under appropriate conditions to obtain a compound of formula VIII (VIII)

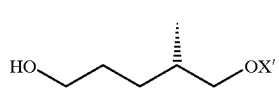

wherein X' is as defined above regarding the compound of formula VII; 6) in a sixth step, reacting the compound obtained in the fifth step with a halogenide of an organic sulfonic acid to obtain a sulfonic acid ester of formula IX (IX)

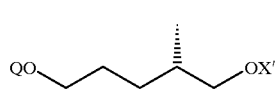

wherein X is an organic sulfonyl moiety; and 7) in a seventh step, reacting the compound obtained in the sixth step with a metal iodide to obtain an iodide compound of formula X;

said compound of formula XX is obtained by a process which comprises: 1) in a first step, reacting a compound of formula XI (XI)

wherein R is as defined above and Hal is halogen, with a trialkyl phosphite to obtain a phosphonate compound of formula XII (XII)

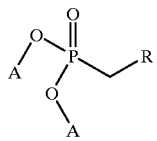

wherein R is as defined above and each A is alkyl; 2) in a second step, reacting the compound obtained in the first step with a compound of formula XV (XV)

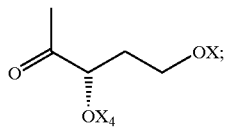

wherein X and $X_4$ are as defined above, in the presence of a strong base to obtain a compound of formula XVII (XVII)

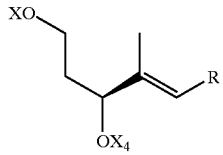

wherein R, X and $X_4$ are as defined above; 3) in a third step, partially de-protecting a compound obtained in the second step under appropriate conditions to obtain a compound of formula XVIII

XVIII

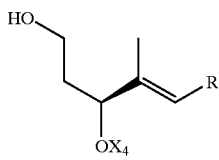

wherein R and $X_4$ are as defined above; 4) in a fourth step, selectively oxidizing a compound obtained in the third step to obtain the corresponding aldehyde of formula XIX (XIX)

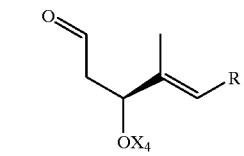

wherein R and $X_4$ are as defined above; and 5) in a fifth step, converting a compound obtained in the fourth step into a compound of formula XX by reacting it with a strong base and iodine in the presence of triphenylphosphonium iodide and then adding the same or a different base;

wherein said compound of formula XV is obtained by a process which comprises: 1) in a first step, reacting (5S)-(2,2-cyclohexylidene)-4-oxo-1,3-dioxolane with $BH_3$-$Me_2S$ complex and $B(OCH_3)_3$ in methanol to obtain 3(S)-dihydro-3-hydroxy-2(3H)-furanone; 2) in a second step, introducing a protecting group $X_4$ in the compound obtained in the first step to obtain a compound of formula XIII (XIII)

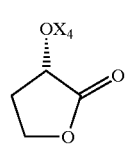

wherein $X_4$ is as defined above; 3) in a third step, reacting a compound obtained in the second step with a methyl metal or methyl metal derivative to obtain a compound of formula XIV (XIV)

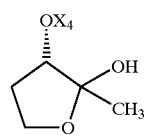

where $X_4$ is as defined above; and 4) in a fourth step, reacting a compound obtained in the third step with a reagent capable of introducing a protecting group to obtain a compound of formula XV;

and (S)-2-(2,2-dimethyl-[1,3]dioxan-4-yl)-2-methyl-pentan-3-one is either prepared by process a) which comprises: 1) in a first step, reacting diethylketone in the presence of zinc dust, $B(OCH_3)_3$ and ethyl-2-bromo-2-methylpropanoate to obtain eithyl-2,2-dimethyl-3-ethyl-3- hydroxypentanoate; 2) in a second step, reacting the compound obtained in the first step with a dehydrating agent to obtain ethyl-(E)-2,2-dimethyl-2-ethyl-3-pentenoate; 3) in a third step, reacting the compound obtained in the second step in the presence of an appropriate complex hydride to obtain (E)-2,2- dimethyl-3-ethyl-3-penten-1ol; 4) in a fourth step, oxidizing the compound obtained in the third step with an appropriate oxidant to obtain (E)-2,2-dimethyl-3-ethyl-3-3-pentenal; 5) in a fifth step, reacting the compound obtained in the fourth step with (S)-(-)-2-hydroxy-1,2,2-triphenyl acetate in the presence of a strong base to obtain (1S)-2,2,1-triphenyl-2-hydroxyethl-(3S,E)-4,4-dimethyl-5-ethyl-3-hydroxy -5-heptenoate; 6) in a sixth step, transforming the compound obtained in the fifth step into (S)-(E)-4,4-dimethyl-5-ethyl-5-heptene-1,3-diol by reacting it with an appropriate complex hydride; 7) in a seventh step, converting the compound obtained in the sixth step into (S)-(E)-2,2-dimethyl- [1,3]-dioxan-4-yl)-3-ethyl-2-methyl-pent-3-ene by reacting it with acetone in the presence of anhydrous copper sulfate, a strong organic acid and a tertiary nitrogen base; and 8) in an eighth step, converting the compound obtained in the seventh step to (S)-2-(2,2-dimethyl-[1,3]dioxan-4-yl)-2-methyl-pentan-3-one by ozonolysis;

or by process b) which comprises: 1) in the first step, reacting (2R)-N-acetylbornane-10,2-sultam in the presence of a dialkylborane triflate or chloride and, after adding a tertiary nitrogen base, with 2,2-dimethyl-3-oxo-pentanol to obtain a sultam compound having the formula

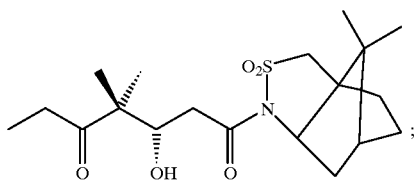

2) in a second step, introducing a protecting group in the compound obtained in the first step by reacting it with an appropriate reagent in the presence of a tertiary nitrogen base to obtain a compound of formula XXI

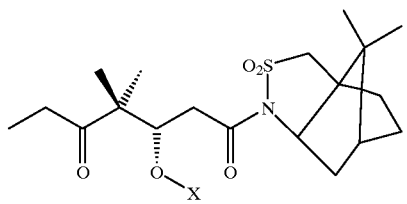

(XXI)

where X is as defined above; 3) in a third step, converting a compound obtained in the second step into the corresponding free acid by reacting it with an appropriate aqueous base to obtain a compound of formula XXII

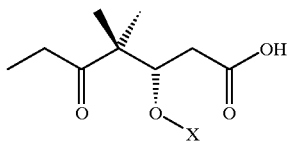

(XXII)

where X is as defined above; 4) in a fourth step, reducing a compound obtained in the third step to obtain a compound of formula XXIII

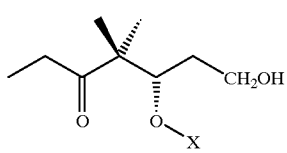

(XXIII)

where X is as defined above; and 5) in a fifth step, de-protecting and transforming a compound obtained in the fourth step by reacting it with an acetone/acid mixture to obtain (S)-2-(2,2-dimethyl- [1,3]dioxan-4-yl)-2-methyl-pentan-3-one.

* * * * *

UNITED STATES PATENT AND TRADEMARK OFFICE
CERTIFICATE OF CORRECTION

PATENT NO.   : 6,350,878 B1                                                    Page 1 of 1
DATED        : February 26, 2002
INVENTOR(S)  : Altmann et al.

It is certified that error appears in the above-identified patent and that said Letters Patent is hereby corrected as shown below:

<u>Title page,</u>
Related U.S. Application Data should read:

-- [63] Continuation of application No. PCT/EP99/03354, filed on May 14, 1999. --

Signed and Sealed this

Third Day of September, 2002

*Attest:*

*Attesting Officer*

JAMES E. ROGAN
*Director of the United States Patent and Trademark Office*